(12) United States Patent
Theus

(10) Patent No.: US 10,238,684 B2
(45) Date of Patent: *Mar. 26, 2019

(54) MICRO- AND NANO-QUANTITY SLEEP ENHANCING NUTRIENT COMPOSITION AND METHOD OF ENHANCING CENTRAL NERVOUS SYSTEM PROTEIN CLEARANCE USING SAME

(71) Applicant: Foundational BioSystems, LLC, Riverwooods, IL (US)

(72) Inventor: Jon Scott Theus, Riverwoods, IL (US)

(73) Assignee: Foundational BioSystems, LLC, Riverwoods, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/287,510

(22) Filed: Oct. 6, 2016

(65) Prior Publication Data

US 2017/0020919 A1 Jan. 26, 2017

Related U.S. Application Data

(63) Continuation-in-part of application No. 12/949,340, filed on Nov. 18, 2010, now Pat. No. 9,549,982.

(51) Int. Cl.
*A61K 31/00* (2006.01)
*A61K 33/00* (2006.01)
(Continued)

(52) U.S. Cl.
CPC .............. *A61K 33/00* (2013.01); *A23L 33/15* (2016.08); *A23L 33/155* (2016.08); *A23L 33/16* (2016.08);
(Continued)

(58) Field of Classification Search
CPC ................................ A61K 31/00; A61K 33/00
See application file for complete search history.

(56) References Cited

U.S. PATENT DOCUMENTS 4,882,167 A 11/1989 Jang .............................. 424/468
5,629,003 A 5/1997 Horstmann et al. .......... 424/401
(Continued)

FOREIGN PATENT DOCUMENTS

WO    WO 1999/017753    4/1999    ............... A61K 9/70

OTHER PUBLICATIONS

CBS News, "CDC: Nearly 9 million Americans use prescription sleep aids" www.cbsnews.com pp. 1-4 (Aug. 29, 2013).
(Continued)

*Primary Examiner* — Rosanne Kosson
(74) *Attorney, Agent, or Firm* — David G. Rosenbaum; J. Peter Paredes; Rosenbaum IP, P.C.

(57) ABSTRACT

The present invention relates to a dietary supplement, composition, nutraceutical, and/or system for inducing or treating biological responses or conditions (namely sleep or sleep disorders) which utilize ultra-low dosage amounts of vitamins, minerals, amino acids, co-enzymes, stimulants, and/or similar ingredients in a highly bio-active delivery system which bypasses first pass metabolism. In particular, the present invention relates to a nutraceutical composition/formulation which substantially bypasses first pass metabolism and such as, but not limited to, activation of the glymphatic system to facilitate clearance of neuronal metabolites from the CSF and interstitial fluids in the brain.

15 Claims, 20 Drawing Sheets

(51) Int. Cl.
A61K 33/14 (2006.01)
A61K 31/192 (2006.01)
A61K 33/24 (2019.01)
A61K 31/4402 (2006.01)
A61K 31/455 (2006.01)
A61K 33/18 (2006.01)
A61K 33/10 (2006.01)
A61K 33/26 (2006.01)
A61K 33/34 (2006.01)
A61K 33/30 (2006.01)
A61K 31/07 (2006.01)
A61K 31/51 (2006.01)
A61K 31/525 (2006.01)
A61K 31/4415 (2006.01)
A61K 31/714 (2006.01)
A61K 31/519 (2006.01)
A61K 31/375 (2006.01)
A61K 31/59 (2006.01)
A61K 31/355 (2006.01)
A61K 31/4188 (2006.01)
A61K 31/122 (2006.01)
A61K 31/198 (2006.01)
A61K 9/00 (2006.01)
A23L 33/16 (2016.01)
A23L 33/155 (2016.01)
A23L 33/175 (2016.01)
A61K 45/06 (2006.01)
A23L 33/15 (2016.01)

(52) U.S. Cl.
CPC .......... *A23L 33/175* (2016.08); *A61K 9/0053* (2013.01); *A61K 31/07* (2013.01); *A61K 31/122* (2013.01); *A61K 31/192* (2013.01); *A61K 31/198* (2013.01); *A61K 31/355* (2013.01); *A61K 31/375* (2013.01); *A61K 31/4188* (2013.01); *A61K 31/4402* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/714* (2013.01); *A61K 33/10* (2013.01); *A61K 33/14* (2013.01); *A61K 33/18* (2013.01); *A61K 33/24* (2013.01); *A61K 33/26* (2013.01); *A61K 33/30* (2013.01); *A61K 33/34* (2013.01); *A61K 45/06* (2013.01); *A23V 2002/00* (2013.01)

(56) References Cited

U.S. PATENT DOCUMENTS

| | | | | |
|---|---|---|---|---|
| 5,948,430 | A | 9/1999 | Zerbe et al. | 424/435 |
| 6,316,029 | B1 | 11/2001 | Jain et al. | 424/484 |
| 6,419,903 | B1 | 7/2002 | Xu et al. | 424/49 |
| 6,569,463 | B2 | 5/2003 | Patel et al. | 424/497 |
| 6,592,887 | B2 | 7/2003 | Zerbe et al. | 424/435 |
| 6,596,298 | B2 | 7/2003 | Leung et al. | 424/435 |
| 7,727,546 | B2 | 6/2010 | Moneymaker et al. | 424/435 |
| 9,060,999 | B2 | 6/2015 | Ferrari | A61K 31/357 |
| 2005/0164987 | A1 | 7/2005 | Barberich | 514/58 |
| 2006/0269619 | A1* | 11/2006 | Moneymaker | A61K 31/00 424/678 |
| 2007/0104762 | A1 | 5/2007 | Roizen | 424/439 |
| 2011/0038957 | A1 | 2/2011 | Fowler | 424/725 |
| 2011/0123507 | A1 | 5/2011 | Moneymaker | 424/94.1 |
| 2016/0243038 | A1 | 8/2016 | Shah | A61K 9/1652 |

OTHER PUBLICATIONS

Cedernaes, J., et al., "Candidate mechanisms underlying the association between sleep-wake disrupstions and Alzheimer's disease" *Sleep Medicine Reviews* pp. 1-10 (2016).

Everson, C., et al., "Antioxidant defense responses to sleep loss and sleep recovery" *Am J Physiol Regul Interr Comp Physiol* 288:R374-R383 (2005).

Halson, S., "Sleep in elite athletes and nutritional interventions to enhance sleep" *Sleep Med* 44:(Suppl 1) S13-S23 (2014).

Kamani, M., et al., "Activation of central Orexin/Hypocretin neurons by dietary amino acids" *Neurons* 72: 619-629 (2011).

Kang, J.E., et al., "Amyloid-β dynamics are regulated by Orexin and the sleep-wake cycle" *Science* 326: 1005-1007 (2009).

Kelsey, N.A., et al., "Nutraceutical antioxidants as novel neuroprotective agents" *Molecules* 15(11): 7792-7814 (2015).

Lichstein, K.L., et al., "Vitamins and sleep: An exploratory study" *Sleep Med* 9(1): 27-32 (2008).

Musiek, E.S., et al., "Sleep, circadian rhythms, and the pathogenesis of Alzheimer disease" *Experimental & Molecular Medicine* 47: 1-8 (2015).

Nair, A., et al., "A simple practice guide for dose conversion between animals and human" *Journal of Basic and Clinical Pharmacy* 7(2): 27-31 (2016).

Norman, A.W., "From vitamin D to hormone D: Fundamentals of the vitamin D endocrine system essential for good health" *Am J Clin Nutr* 88(suppl): 491S-499S (2008).

Salin-Pascual, R., et al., "Hypothalamic regulation of sleep" *Neuropsychopharmacology* 25(S5): S21-S27 (2001).

Saper, C.B., et al., "Hypothalamic regulation of sleep and circadian rhythms" *Nature* 437: 1257-1263 (2005).

Tarasoff-Conway, J.M., et al., "Clearance systems in the brain—implications for Alzheimer disease" *Nat Rev Neurol* 11(8): 457-470 (2015).

Xie, L., et al., "Sleep drives metabolite clearance from the adult brain" *Science* 342(6156): 373-377 (2013).

International Search Report, PCT Application No. PCT/US17/55655, pp. 1-3 (dated Feb. 2, 2018).

* cited by examiner

MICRO- AND NANO-QUANTITY SLEEP ENHANCING NUTRIENT COMPOSITION AND METHOD OF ENHANCING CENTRAL NERVOUS SYSTEM PROTEIN CLEARANCE USING SAME

RELATED APPLICATIONS

This application is a continuation-in-part of co-pending commonly assigned U.S. patent application Ser. No. 12/949,340 filed on Nov. 18, 2010 and published as U.S. Published Patent Application No. 2011-0123507 on May 26, 2011, the content of which is incorporated by reference in its entirety.

FIELD OF THE INVENTION

The present invention pertains generally to a composition and method that enhances the quality of sleep. More particularly, the present invention pertains to a composition of micro- and nano-quantities of vitamins, minerals, antioxidants and amino acids in a pharmacologically acceptable carrier adapted for administration to a mammal in need thereof by a route of administration that substantially avoids first pass metabolism. Still more particularly, the present invention is directed to a composition and method of use of the composition that enhances clearance of proteins from the brain or cerebrospinal fluid that have been implicated in neurodegenerative disorders.

The present invention also relates generally to individualized responsive dosing dietary supplement systems, compositions, methods of treatment, and processes of producing the same, which allow a consumer or patient to regulate native biological or physiological processes, conditions or responses to enhance sleep duration and sleep quality while reducing the incidence of sleep disorders interfering with sleep duration or quality.

BACKGROUND

A relationship between diminished sleep qualities, decreased cognitive function and increased risk of certain neurodetenerative disorders, such as Alzheimer disease has been recently identified. The association between sleep quality and Alzheimer disease has been found to be bidirectional, i.e., sleep disturbances are a comorbidity of Alzheimer disease and decreases in sleep quality are associated with an increase in severity of Alzheimer disease pathology. In the specific case of Alzheimer disease soluble β-amyloid is measurable in cerebrospinal fluid ("CSF") and interstitial fluid, with the level of soluble β-amyloid correlating with the extent of plaque deposition of insoluble β-amyloid in the brain. Brown, B. M., et al., *The Relationship between Sleep Quality and Brain Amyloid Burden*, SLEEP 39(5), 2016, p. 1063. Brown, et al. specifically found a correlation between sleep latency (the time to fall asleep) and β-amyloid burden in its study, but were careful to contrast their results with other studies that found an absence of such correlation.

Recently, researchers identified the glymphatic system, a system managed by the brain's glial cells that expand and contract to control the flow of CSF and clearing of soluble β-amyloid present in the CSF. During deep sleep, particularly stage 3, non-REM, slow wave sleep, the glymphatic system is activated to allow the brain to rid itself of β-amyloid and other waste products, including proteins such as tau protein and α-synuclean, peptides, lactate or ammonia that are the product of neuronal metabolism and present in the interstitial fluid around the brain cells. Nedergaard, M., *Sleep Drives Metabolic Clearance from the Adult Brain*, (Science Vol 342, Oct. 18, 2013, p. 373-377.

Astrocytes, star-shaped glial cells, express aquaporin 4 water channel (AQP4). Penetrating arteries which end in the brain are covered by astrocytic end feet which express AQP4. This perivascular space around the arteries is a mechanism that permits rapid influx observable with tracer. CSF first passes from the pariarterial space, through the aquaporin 4 (AQP4) water channels, into the interstitial space, where waste products are driven by convective flux toward the veins. The CSF exchanges with interstitial fluid containing waste products (such as, for example, β-amyloid, tau, α-synuclean, etc.), the interstitial fluid then enters the paravenous space, eventually reaching lymphatic vessels in the neck, and later the systemic circulation, where the proteins travel to the liver, where they are metabolized.

In this way the brain eliminates waste products of neuronal metabolism during n3, non-REM, slow wave sleep by expanding the interstitial fluid volume which effectively washes away the waste products in the interstitial fluid. Failure to remove these waste products, including β-amyloid and tau proteins implicated in Alzheimer disease and α-synuclean implicated in Parkinson's disease.

In healthy adults, sleep typically begins with NREM sleep. The pattern of clear rhythmic alpha activity associated with wakefulness gives way to N1, the first stage of sleep, which is defined by a low-voltage, mixed-frequency pattern. The transition from wakefulness to N1 occurs seconds to minutes after the start of the slow eye movements seen when a person first begins to nod off. This first period of N1 typically lasts just one to seven minutes. The second stage, or N2, which is signaled by sleep spindles and/or K complexes in the EEG recording, comes next and generally lasts 10 to 25 minutes. As N2 sleep progresses, there is a gradual appearance of the high-voltage, slow-wave activity characteristic of N3, the third stage of NREM sleep. This stage, which generally lasts 20 to 40 minutes, is referred to as "slow-wave," "delta," or "deep" sleep. As NREM sleep progresses, the brain becomes less responsive to external stimuli, and it becomes increasingly difficult to awaken an individual from sleep.

Following the N3 stage of sleep, a series of body movements usually signals an "ascent" to lighter NREM sleep stages. Typically, a 5- to 10-minute period of N2 precedes the initial REM sleep episode. REM sleep comprises about 20 to 25 percent of total sleep in typical healthy adults. NREM sleep and REM sleep continue to alternate through the night in a cyclical fashion. Most slow-wave NREM sleep occurs in the first part of the night; REM sleep episodes, the first of which may last only one to five minutes, generally become longer through the night. During a typical night, N3 sleep occupies less time in the second cycle than the first and may disappear altogether from later cycles. The average length of the first NREM-REM sleep cycle is between 70 and 100 minutes; the average length of the second and later cycles is about 90 to 120 minutes.

The hypothalamus is anatomically positioned adjacent the third ventricle of the brain. Without intending to be bound to theory, it is believed, that by signaling the hypothalamus to activate sleep, and in particular n3 stage non-REM sleep, the glymphatic system is then regulated to increase CSF flux throughout the brain ventricles, with the resulting effect of increasing the glymphatic clearing of potentially deleterious proteins and other molecules present in the CSF and interstitial fluid. Assuming this to be the case, it is theorized by the present inventors that administration of a composition capable of substantially avoiding first pass metabolism, crossing the blood-brain barrier, and acting on the hypothalamus to stimulate sleep, and in particular n3 stage non-REM sleep, has the effect of increasing glymphatic activity and, therefore, clearing the metabolic waste products of neuronal metabolism from the brain and not allowing them to accumulate and form deleterious plaques implicated in various neuro-degenerative disorders.

Vitamins, minerals, amino acids, and co-enzymes are compounds required by an animal, mammalian or human body in small amounts for metabolism, biophysiological repair, to protect health, and for proper growth and cellular reproduction. These compounds also assist in the formation of hormones, blood cells, nervous-system chemicals, and genetic material. Vitamins, minerals, amino acids, and co-enzymes are often referred to as nutrients, defined herein as a substance or ingredient which may be found in food which imparts a medicinal or health benefit. The various nutrient compounds are not chemically related, and most differ in their physiological actions. They generally act as catalysts, combining with proteins to create metabolically active enzymes that in turn produce hundreds (or more) of important chemical reactions throughout the body. Without nutrients, many of these reactions would slow down or cease. The intricate ways in which nutrients act on the body (e.g., positive and negative feedback regulatory processes), however, are still far from clear.

Dietary supplements are generally nutrient mixtures commonly taken in single mega-dose dosage forms which contain vitamin, mineral and other nutrient doses. Although mega-dose regimens are a common practice for the prevention of disease, there is a great deal of debate in the conventional literature regarding the efficacy of such regimens. Moreover, consuming large doses of vitamins, minerals, or other nutrients, in the absence of some deficiency or without proper medical supervision, may cause harmful toxic effects and/or result in hypervitaminosis.

Additionally, a consumer usually has little choice in choosing the variety of ingredients, dosage levels, or dosing regimens of a conventional dietary supplement, such as a standard vitamin tablet. Conventional dietary supplements may be effective for a general purpose, but can provide an excess of vitamins, minerals, stimulants, or other compounds which a consumer does not desire, or those supplements may not adequately target an individual's specific dietary need or desired biological response. Additionally, conventional dosage forms of dietary supplements only allow a consumer to take one or two doses per 24 hour period. As a result, conventional dietary supplements fail to recognize that the physiological state and resultant nutrient requirements of any single individual can depend upon and fluctuate based upon a number of different biophysical variables during the course of each day or dosing regimen. For example, individual variations in diet, and the amount and intensity of physical activity, provide physical and chemical stimuli that stress various systems of the body to differing degrees from one person to the next and for each of those individuals on any given day. Thus, standard "one size fits all" mega-dose dosage forms/regimens are not amenable to empirical dosage adjustment to achieve an individualized biophysiological objective or response such as, but not limited to, enhanced sleep quality, initiation of sleep, sleep maintenance, and the like.

Another drawback with most conventional dietary supplements is that they suffer from poor degrees and/or rates at which the various nutrients are absorbed into the systemic circulation of the body and made available for biophysiological activity (e.g., "bioavailability"). These degrees or rates of bioavailability typically depend upon the dose, dosage form, and method of administration.

One particular barrier to efficient nutrient bioavailability is "first-pass metabolism" or, synonymously "first-pass effect." First-pass metabolism is generally understood by those in the field of pharmacology to mean the intestinal and/or hepatic degradation or alteration of a substance taken by mouth, which after absorption, removes some of the active substance from the blood before it enters the general circulation and is available to the body. Alternatively, first-pass metabolism is understood to mean a process in which the nutrient compound(s) are modified, activated, or inactivated before they enter the systemic circulation, or are left unchanged and excreted.

For example, it is generally understood by those skilled in at least the nutraceutical and/or supplements field that one significant drawback to "mega-dosing" of vitamins and minerals is that increased dosages may not be adequately absorbed into the body, or may actually decrease absorption. Thus, available transport mechanisms may become saturated and unable to absorb the excess dose of the vitamin, mineral, or other nutrient. Additionally, a drawback to vitamin or mineral delivery via a conventional tablet or capsule is that differences in luminal pH along the gastrointestinal tract lining, surface area per luminal volume, blood perfusion, presence of bile and mucus, and the nature of epithelial membranes may prevent or alter efficient absorption, activation, and the like of a nutrient, thereby decreasing its bioavailability and subsequent usage by the human body.

To compensate for first pass metabolism effects, some previous efforts have been directed to enteric coated tablet or capsule dosage forms which pass through the stomach unaltered to disintegrate in the lower intestines. However, aside from a delayed biophysiological response as gastric emptying becomes rate-limiting, gastric irritability, and potential allergic reactions from the ingestion of such coating materials occurs, and these enteric coated delayed release dosage forms dissolve and are absorbed within a narrow time frame. As a result, the body typically excretes the non-absorbed vitamins or minerals.

Additional previous attempts in addressing the challenge of bypassing first pass metabolism have been directed to continuous or gradual release dosage forms. U.S. Pat. No. 4,882,167, to Jang, discloses dry direct compressed products for controlled release of actives including vitamins or minerals. However, there still remains the challenge of a composition having ultra-low dosage amounts of vitamins or minerals, dosing flexibility, or alternatively systems, compositions, or methods for individualized responsive dosing based on at least one desired biological response such as increased sleep quality or treatment of a sleep disorder.

WO 99/17753 (to Awamura et al.) discloses rapidly dissolving films for delivery of drugs to be adsorbed in the digestive tract. U.S. Pat. No. 6,596,298, to Leung, discloses consumable oral care films which may optionally contain active amounts of pharmaceutical drugs. However, there still remains the challenge of utilizing vitamins or minerals, and more specifically, ultra-low dosage amounts of nutrients which would operate to provide flexibility for individualized dosing, especially in the promotion, enhancement or improvement in sleep initiation, maintenance, and/or quality. Moreover, these products or processes do not provide a system or selection for varying the type or level of dosage depending on a biological response desired, such as a focus upon sleep.

Therefore, there is presently a need for an efficient process for producing a nutrient dosage and delivery system that is capable of individualized biological response dosing (i.e., dosing based upon empirical analysis and adjustment in response to a desired biological outcome such as enhanced sleep quality and the like), which is available in a suitable dosage form, and preferably is efficiently absorbed and made bioavailable to animal or human tissue. Additionally, there is presently a need for a treatment method for managing finely tuned biological needs and responses which utilizes micro- and nano-quantities of the actives in ultra-low dosage amounts, substantially avoids first pass metabolism, and allows for varied dosage/dosing regimens within each dosing period (e.g., 24 hours, 6 hours, 1 hour). Furthermore, there exists a present need for an ultra-low dose nutraceutical having micro- and nano-quantities of actives that substantially avoids first pass metabolism, and which increases n3 stage non-REM sleep and glymphatic system activation to allow for clearing of neuronal metabolites from the CSF and interstitial brain fluids.

SUMMARY OF THE INVENTION

In at least one aspect, the present invention provides a nutraceutical composition comprising at least two of the following in a single dose volume of about 0.25 milliliters: about $5.45 \times^{-7}$ g magnesium chloride; about $8.17 \times^{-7}$ g sodium ascorbate; about $8.17 \times^{-7}$ g potassium carbonate; about $5.45 \times^{-7}$ g calcium ascorbate; about $4.54 \times^{-6}$ g ascorbic acid (ester C); about $8.62 \times^{-7}$ g caffeine; about $9.08 \times^{-8}$ g niacin; about $4.08 \times^{-7}$ g potassium benzoate; about $1.70 \times^{-9}$ g chromium picolinate; about $1.70 \times^{-9}$ g chromium polynicotinate; about $5.67 \times^{-7}$ g coenzyme Q-10; about $2.27 \times^{-6}$ g L-glutamine; about $2.27 \times^{-6}$ g L-arginine; about $9.08 \times^{-7}$ g potassium sorbate; about $6.58 \times^{-7}$ g sodium nitrite; about $9.36 \times^{-8}$ g vitamin A; about 1.64×g vitamin B1; about 1.24×g vitamin B2; about $1.58 \times^{-8}$ g vitamin B3; about $1.58 \times^{-8}$ g vitamin B6; about $4.73 \times^{-12}$ g vitamin B12; about $4.73 \times^{-8}$ g vitamin C; about $7.48 \times^{-9}$ g vitamin D3; about $5.46 \times^{-10}$ g vitamin E; about $1.42 \times^{-10}$ g vitamin H; about $1.51 \times^{-10}$ g folic acid; about $6.93 \times^{-10}$ g copper; about $6.02 \times^{-9}$ g iron; about 5.18 g potassium iodide; about $3.15 \times^{-8}$ g calcium carbonate; or about $5.07 \times^{-9}$ g zinc.

In another aspect, a nutraceutical composition of the present invention is provided to an individual to induce enhanced sleep quality in the individual. The enhanced sleep quality outcomes of the present invention may be characterized by an outcome selected from the group consisting essentially of decreased ratio of stage 1 sleep to DELTA sleep, decreased ratio of stage 1 sleep to REM sleep, decreased number of awakenings, decreased number of arousals, decreased latencies, increased levels of blood oxygen saturation, and a decreased number of sleep disorder events. The decreased number of sleep disorder event outcomes of the present invention may be a decreased number of apneaic events.

In an additional aspect, a nutraceutical composition of the present invention may function to induce enhanced sleep quality through a non-systemic, central mechanism.

In a further aspect, a nutraceutical composition of the present invention is provided to an individual via an administration route that substantially avoids first pass metabolism. An administration route of the present invention may be selected from the group consisting essentially of sublingual, buccal, nasal, transdermal, intradermal, intramuscular, intravenous and rectal routes.

In certain aspects, a nutraceutical composition of the present invention may further comprise at least one additive. Additives that are compatible with the present invention may be present in amounts from about $2 \times^{-4}$ grams to about $1.5 \times^{-2}$ grams of at least one dose of the nutraceutical.

In additional aspects, a nutraceutical composition of the present invention may be provided in a dosage form selected from the group consisting of parenteral, sublingual liquid, oral film, liquid, lozenge, ampoule, troche, suppository, transdermal patch, nasal spray, dragée, slurry, suspension, emulsion, injectable, and intravenous solution.

In another aspect, the present invention provides a method of improving sleep quality or treating a sleep disorder comprising administering a nutraceutical composition of the present invention. The method of improving sleep quality or treating a sleep disorder of the present invention may be characterized by an outcome selected from the group consisting of decreased ratio of stage 1 to DELTA sleep, decreased ratio of stage 1 to REM sleep, decreased number of apneas, decreased apnea index, decreased number of arousals, decreased arousal index, decreased number of awakenings, and increased levels of blood oxygen saturation.

In an additional aspect, the method of improving sleep quality or treating a sleep disorder of the present invention is achieved by administering a nutraceutical composition of the present invention to a subject in need thereof in a volume of about 0.25 milliliters.

In a further aspect, the method of improving sleep quality or treating a sleep disorder of the present invention is achieved by administering a nutraceutical composition of the present invention to a subject in need thereof in a volume of about 0.30 milliliters.

In at least one additional aspect, the present invention provides a nutraceutical composition comprising at least two of the following in a single dose volume of about 0.25 milliliters: about $3.61 \times^{-7}$ g magnesium chloride; about $5.42 \times^{-7}$ g sodium ascorbate; about $5.42 \times^{-7}$ g potassium carbonate; about $3.61 \times^{-7}$ g calcium ascorbate; about $3.01 \times^{-6}$ g ascorbic acid (ester C); about $5.72 \times^{-7}$ g caffeine; about $6.02 \times^{-8}$ g niacin; about $2.71 \times^{-7}$ g potassium benzoate; about $1.13 \times^{-9}$ g chromium picolinate; about 1.13×g chromium polynicotinate; about $3.76 \times^{-7}$ g coenzyme Q-10; about $1.51 \times^{-6}$ g L-glutamine; about $1.51 \times^{-9}$ g L-arginine; about $6.02 \times^{-7}$ g potassium sorbate; about $4.37 \times^{-7}$ g sodium nitrite; about $6.21 \times^{-8}$ g vitamin A; about $1.09 \times^{-9}$ g vitamin B1; about $8.20 \times^{-10}$ g vitamin B2; about $1.05 \times^{-8}$ g vitamin B3; about $1.05 \times^{-8}$ g vitamin B6; about $3.14 \times^{-12}$ g vitamin B12; about $3.14 \times^{-8}$ g vitamin C; about $4.97 \times^{-9}$ g vitamin D3; about $3.62 \times^{-10}$ g vitamin E; about $9.41 \times^{11}$ g vitamin H; about $1.00 \times^{-10}$ g folic acid; about $4.60 \times^{-10}$ g copper; about $3.99 \times^{-9}$ g iron; about $3.44 \times^{11}$ g potassium iodide; about $2.09 \times^{-8}$ g calcium carbonate; or about $3.37 \times^{-9}$ g zinc.

In a further aspect, a nutraceutical composition of the present invention may be provided to an individual to induce short duration sleep. The induced short duration sleep of the present invention may last for about one hour or less.

In another aspect, the present invention provides a nutraceutical composition comprising at least two of the following in a single dose volume of about 0.25 milliliters: about $9.11 \times^{-8}$ g magnesium chloride; about $1.37 \times^{-7}$ g sodium ascorbate; about $1.37 \times^{-7}$ g potassium carbonate; about $9.11 \times^{-8}$ g calcium ascorbate; about $7.59 \times^{-7}$ g ascorbic acid (ester C); about $1.44 \times^{-7}$ g caffeine; about $1.52 \times^{-8}$ g niacin; about $6.84 \times^{-8}$ g potassium benzoate; about $2.84 \times^{-10}$ g chromium picolinate; about $2.84 \times^{-10}$ g chromium polynicotinate; about $9.49 \times^{-8}$ g coenzyme Q-10; about $3.80 \times^{-7}$ g L-glutamine; about $3.80 \times^{-7}$ g L-arginine; about $1.52 \times^{-7}$ g potassium sorbate; about $1.10 \times^{-7}$ g sodium nitrite; about $1.57 \times^{-8}$ g vitamin A; about $2.74 \times^{-10}$ g vitamin B1; about $2.07 \times^{-10}$ g vitamin B2; about $2.64 \times^{-9}$ g vitamin B3; about $2.64 \times^{-9}$ g vitamin B6; about $7.91 \times^{-13}$ g vitamin B12; about $7.91 \times^{-9}$ g vitamin C; about $1.25 \times^{-9}$ g vitamin D3; about $9.13 \times^{11}$ g vitamin E; about 2.37 g vitamin H; about $2.53 \times^{11}$ g folic acid; about $1.16 \times^{-10}$ g copper; about $1.01 \times^{-9}$ g iron; about $8.66 \times^{-12}$ g potassium iodide; about $5.27 \times^{-9}$ g calcium carbonate; or about $8.49 \times^{-10}$ g zinc.

In an additional aspect, the present invention provides a nutraceutical composition comprising at least two of the following in a single dose volume of about 0.25 milliliters: about $6.08 \times^{-8}$ g magnesium chloride; about $9.12 \times^{-8}$ g sodium ascorbate; about $9.12 \times^{8}$ g potassium carbonate; about $6.08 \times^{-8}$ g calcium ascorbate; about $5.07 \times^{-7}$ g ascorbic acid (ester C); about $9.63 \times^{-8}$ g caffeine; about $1.01 \times^{-8}$ g niacin; about $4.56 \times^{-8}$ g potassium benzoate; about $1.89 \times^{-10}$ g chromium picolinate; about $1.89 \times^{-10}$ g chromium polynicotinate; about $6.33 \times^{-8}$ g coenzyme Q-10; about $2.53 \times^{-7}$ g L-glutamine; about $2.53 \times^{-7}$ g L-arginine; about $1.01 \times^{-7}$ g potassium sorbate; about $7.35 \times^{-8}$ g sodium nitrite; about $1.04 \times^{-8}$ g vitamin A; about $1.83 \times^{-10}$ g vitamin B1; about $1.38 \times^{-10}$ g vitamin B2; about $1.76 \times^{-9}$ g vitamin B3; about $1.76 \times^{-9}$ g vitamin B6; about $5.28 \times^{-13}$ g vitamin B12; about $5.28 \times^{-9}$ g vitamin C; about $8.36 \times^{-10}$ g vitamin D3; about $6.09 \times^{11}$ g vitamin E; about $1.58 \times^{11}$ g vitamin H; about $1.69 \times^{11}$ g folic acid; about $7.74 \times^{11}$ g copper; about $6.72 \times^{-10}$ g iron; about $5.78 \times^{-12}$ g potassium iodide; about $3.52 \times^{-9}$ g calcium carbonate; or about $5.66 \times^{-10}$ g zinc.

In an additional aspect, the present invention provides a nutraceutical composition comprising at least five vitamins or minerals; wherein at least one dose of the nutraceutical comprises from about $1.25 \times 10^{-13}$ grams to about $3.5 \times 10^{-3}$ grams of at least one mineral, from about $6 \times^{-9}$ grams to about $6 \times 10^{-6}$ grams of at least one enzyme, from about $2 \times 10^{-14}$ grams to about $1.8 \times^{-4}$ grams of at least one vitamin, from about $3 \times^{-8}$ grams to about $3 \times -4$ grams of at least one adjunct, and from about $1.5 \times^{-8}$ grams to about $1.5 \times^{-2}$ grams of at least one amino acid; wherein the nutraceutical/supplement composition is provided to an individual via an administration route that substantially avoids first pass metabolism; and wherein the nutraceutical/supplement composition is provided to an individual to induce enhanced sleep quality or sleep quality outcomes in the individual.

In another aspect, the present invention provides a nutraceutical/supplement composition comprising at least five vitamins or minerals; wherein at least one dose of the nutraceutical/supplement composition comprises from about $3 \times^{-8}$ grams to about $3 \times^{-4}$ grams of at least one stimulant, from about $1.25 \times^{-13}$ grams to about $3.5 \times^{-3}$ grams of at least one mineral, from about $6 \times^{-9}$ grams to about $6 \times^{-6}$ grams of at least one enzyme, from about $2 \times^{-14}$ grams to about $1.8 \times^{-4}$ grams of at least one vitamin, and from about $1.5 \times^{-8}$ grams to about $1.5 \times^{-2}$ of at least one amino acid; wherein the nutraceutical/supplement composition is provided to an individual via an administration route that substantially avoids first pass metabolism; and wherein the nutraceutical/supplement composition is provided to an individual to induce decreased sleep latency time and/or increased sleep time duration in the individual.

In a further aspect, the present invention provides a nutraceutical/supplement composition comprising at least five vitamins or minerals; wherein at least one dose of the nutraceutical/supplement comprises from about $1.25 \times^{-13}$ grams to about $3.5 \times^{-3}$ grams of at least one mineral, from about $6 \times^{-9}$ grams to about $6 \times^{-6}$ grams of at least one enzyme, from about $2 \times^{-14}$ grams to about $1.8 \times^{-4}$ grams of at least one vitamin, from about $3 \times^{-8}$ grams to about $3 \times^{-4}$ grams of at least one adjunct, and from about $1.5 \times^{-8}$ grams to about $1.5 \times^{-2}$ grams of at least one amino acid; wherein the nutraceutical/supplement is provided to an individual via an administration route that substantially avoids first pass metabolism; and wherein the nutraceutical/supplement is provided to an individual to treat a sleep disorder, for example, sleep apnea.

In an additional aspect, the present invention provides a method of improving sleep quality or treating a sleep disorder comprising administering a nutraceutical/supplement composition comprising at least five vitamins or minerals to an individual; wherein at least one dose of the nutraceutical/supplement comprises from about $3 \times^{-8}$ grams to about $3 \times^{-4}$ grams of at least one stimulant, from about $1.25 \times^{-13}$ grams to about $3.5 \times^{-3}$ grams of at least one mineral, from about $6 \times^{-9}$ grams to about $6 \times^{-6}$ grams of at least one enzyme, from about $2 \times^{-14}$ grams to about $1.8 \times^{-4}$ grams of at least one vitamin, and from about $1.5 \times^{-8}$ grams to about $1.5 \times^{-2}$ grams of at least one amino acid; wherein the nutraceutical/supplement is provided to the individual via an administration route that substantially avoids first pass metabolism; wherein the enhanced sleep quality or sleep disorder treatment is characterized by an outcome such as, but not limited to decreased ratio of stage 1 to DELTA sleep, decreased ratio of stage 1 to REM sleep, decreased number of apneas, decreased apnea index, decreased number of arousals, decreased arousal index, decreased number of awakenings, and increased levels of blood oxygen saturation; and wherein the nutraceutical/supplement functions to induce the sleep related outcome through a non-systemic, central mechanism.

In another aspect, the present invention provides a nutraceutical/supplement composition comprising at least five vitamins or minerals; wherein at least one dose of the nutraceutical/supplement composition comprises magnesium chloride, sodium ascorbate, potassium carbonate, calcium ascorbate, potassium sorbate, sodium nitrite, potassium benzoate, chromium picolinate, chromium polynicotinate, copper, iron, potassium iodide, calcium carbonate, zinc, ascorbic acid, niacin, vitamin A, vitamin B1, vitamin B2, vitamin B3, vitamin B6, vitamin B12, vitamin C, vitamin D3, vitamin E, vitamin H, folic acid, caffeine, co-enzyme Q-10, l-arginine, l-glutamine, and combinations and derivatives thereof; wherein the nutraceutical/supplement is provided to an individual via an administration route that substantially avoids first pass metabolism; and wherein the nutraceutical/supplement is provided to an individual to induce enhanced sleep quality in the individual.

In yet another aspect, the present invention provides a nutraceutical/supplement composition for enhancing sleep quality and/or treating a sleep disorder (e.g., sleep apnea, interrupted sleep, difficult sleep initiation, sleep latency disorder, among others); wherein at least one dose of the nutraceutical comprises from about $8.65824 \times^{-8}$ grams to about $9.56963 \times^{-8}$ grams of magnesium chloride, from about $1.29874 \times^{-7}$ grams to about $1.43544 \times^{-7}$ grams of sodium ascorbate, from about $1.29874 \times^{-7}$ grams to about $1.43544 \times^{-7}$ grams potassium carbonate, from about $8.65824 \times^{-8}$ grams to about $9.56963 \times^{-8}$ grams of calcium ascorbate, from about $7.2152 \times^{-7}$ grams to about $7.97469 \times^{-7}$ grams of ascorbic acid (ester C), from about $1.37089 \times^{-7}$ grams to about $1.51519 \times^{-7}$ grams of caffeine, from about $1.44304 \times^{-8}$ grams to about $1.59494 \times^{-8}$ grams of niacin, from about $6.49368 \times^{-8}$ grams to about $7.17722 \times^{-8}$ grams of potassium benzoate, from about $2.69848 \times^{-10}$ to about $2.98254 \times^{-10}$ grams of chromium picolinate, from about $2.69848 \times^{-10}$ grams to about $2.98254 \times^{-10}$ grams of chromium polynicotinate, from about $9.019 \times^{-8}$ grams to about $9.96837 \times^{-8}$ grams of coenzyme Q10, from about $3.6076 \times^{-7}$ grams to about $3.98735 \times^{-7}$ grams of L-glutamine, from about $3.6076 \times^{-7}$ grams to about $3.98735 \times^{-7}$ grams L-arginine, from about $1.44304 \times^{-7}$ grams to about $1.59494 \times^{-7}$ grams of potassium sorbate, from about $1.0462 \times^{-7}$ grams to about $1.15633 \times^{-7}$ grams of sodium nitrite, from about $1.48762 \times^{-8}$ grams to about $1.64421 \times^{-8}$ grams of vitamin A, from about $2.60048 \times^{-10}$ to about $2.87421 \times^{-10}$ grams of vitamin B1, from about $1.96414 \times^{-10}$ grams to about $2.17089 \times^{-10}$ grams of vitamin B2, from about $2.50528 \times^{-9}$ grams to about $2.76899 \times^{-9}$ grams of vitamin B3, from about $2.50528 \times^{-9}$ grams to about $2.76899 \times^{-9}$ grams of vitamin B6, from about $7.51583 \times^{-13}$ grams to about $8.30697 \times^{-13}$ grams of vitamin B12, from about $7.51583 \times^{-9}$ grams to about $8.30697 \times^{-9}$ grams of vitamin C, from about $1.19009 \times^{-9}$ grams to about $1.31537 \times^{-9}$ grams of vitamin D3, from about $8.67776 \times^{11}$ grams to about $9.59121 \times^{11}$ grams of vitamin E, from about $2.25475 \times^{11}$ grams to about $2.49209 \times^{11}$ grams of vitamin H, from about $2.40507 \times^{11}$ grams to about $2.65823 \times^{11}$ grams of folic acid, from about $1.10232 \times^{-10}$ grams to about $1.21836 \times^{-10}$ grams of copper, from about $9.57016 \times^{-10}$ grams to about $1.05775 \times^{-9}$ grams of iron, from about $8.23016 \times^{-12}$ grams to about $9.0965 \times^{-12}$ grams of potassium iodide, from about $5.01055 \times^{-9}$ grams to about $5.53798 \times^{-9}$ grams of calcium carbonate, and from about $8.06699 \times^{-10}$ grams to about $8.91615 \times^{-10}$ grams of zinc; and wherein the nutraceutical/supplement composition is provided to an individual via an administration route that substantially avoids first pass metabolism.

In a further aspect, the present invention provides a nutraceutical/supplement composition for enhancing short-time duration sleep; wherein at least one dose of the nutraceutical/supplement composition comprises from about $5.77505 \times^{-8}$ grams to about $6.38294 \times^{-8}$ grams of magnesium chloride, from about $8.66257 \times^{-8}$ grams to about $9.57442 \times^{-8}$ grams of sodium ascorbate, from about $8.66257 \times^{-8}$ grams to about $9.57442 \times^{-8}$ grams of potassium carbonate, from about $5.77505 \times^{-8}$ grams to about $6.38294 \times^{-8}$ grams of calcium ascorbate, from about $4.81254 \times^{-7}$ grams to about $5.31912 \times^{-7}$ grams of ascorbic acid (also known as ester C), from about $9.14382 \times^{-8}$ grams to about $1.01063 \times^{-7}$ grams of caffeine, from about $9.62508 \times^{-9}$ grams to about $1.06382 \times^{-8}$ grams of niacin, from about $4.33128 \times^{-8}$ grams to about $4.78721 \times^{-8}$ grams of potassium benzoate, from about $1.79989 \times^{-10}$ grams to about $1.98935 \times^{-10}$ grams of chromium picolinate, from about $1.79989 \times^{-10}$ grams to about $1.98935 \times^{-10}$ grams of chromium polynicotinate, from about $6.01567 \times^{-8}$ grams to about $6.6489 \times^{-8}$ grams of coenzyme Q10, from about $2.40627 \times^{-7}$ grams to about $2.65956 \times^{-7}$ grams of L-glutamine, from about $2.40627 \times^{-7}$ grams to about $2.65956 \times^{-7}$ grams of L-arginine, from about $9.62508 \times^{-8}$ grams to about $1.06382 \times^{-7}$ grams of potassium sorbate, from about $6.97818 \times^{-8}$ grams to about $7.71272 \times^{-8}$ grams of sodium nitrite, from about $9.9224 \times^{-9}$ grams to about $1.09669 \times^{-8}$ grams of vitamin A, from about $1.73452 \times^{-10}$ grams to about $1.9171 \times^{-10}$ grams of vitamin B1, from about $1.31008 \times^{-10}$ grams to about $1.44798 \times^{-10}$ grams of vitamin B2, from about $1.67102 \times^{-9}$ grams to about $1.84692 \times^{-9}$ grams of vitamin B3, from about $1.67102 \times^{-9}$ grams to about $1.84692 \times^{-9}$ grams of vitamin B6, from about $5.01306 \times^{-13}$ grams to about $5.54075 \times^{-13}$ grams of vitamin B12, from about $5.01306 \times^{-9}$ grams to about $5.54075 \times^{9}$ grams of vitamin C, from about $7.93792 \times^{-10}$ grams to about $8.77349 \times^{-10}$ grams of vitamin D3, from about $5.78806 \times^{11}$ grams to about $6.39733 \times^{11}$ grams of vitamin E, from about $1.50392 \times^{11}$ grams to about $1.66223$ grams of vitamin H, from about $1.60418 \times^{11}$ grams to about $1.77304 \times^{11}$ grams of folic acid, from about $7.35249 \times^{11}$ grams to about $8.12643 \times^{11}$ grams of copper, from about $6.3833 \times^{-10}$ grams to about $7.05522 \times^{-10}$ grams of iron, from about $5.48952 \times^{-12}$ grams to about $6.06736 \times^{-12}$ grams of potassium Iodide, from about $3.34204 \times^{-9}$ grams to about $3.69383 \times^{-9}$ grams of calcium carbonate, and from about $5.38068 \times^{-10}$ grams to about $5.94707 \times^{-10}$ grams of zinc; and wherein the nutraceutical/supplement composition is provided to an individual via an administration route that substantially avoids first pass metabolism.

Additional embodiments are disclosed in the detailed description provided below. While the presently described technology will be provided in connection with one or more preferred embodiments, it will be understood by those skilled in the art that the presently described technology is not limited to those embodiments. To the contrary, the presently described technology includes all alternatives, modifications, and equivalents as may be included within the spirit and scope of the appended claims.

DETAILED DESCRIPTION OF THE INVENTION

Definitions

Figure 1:
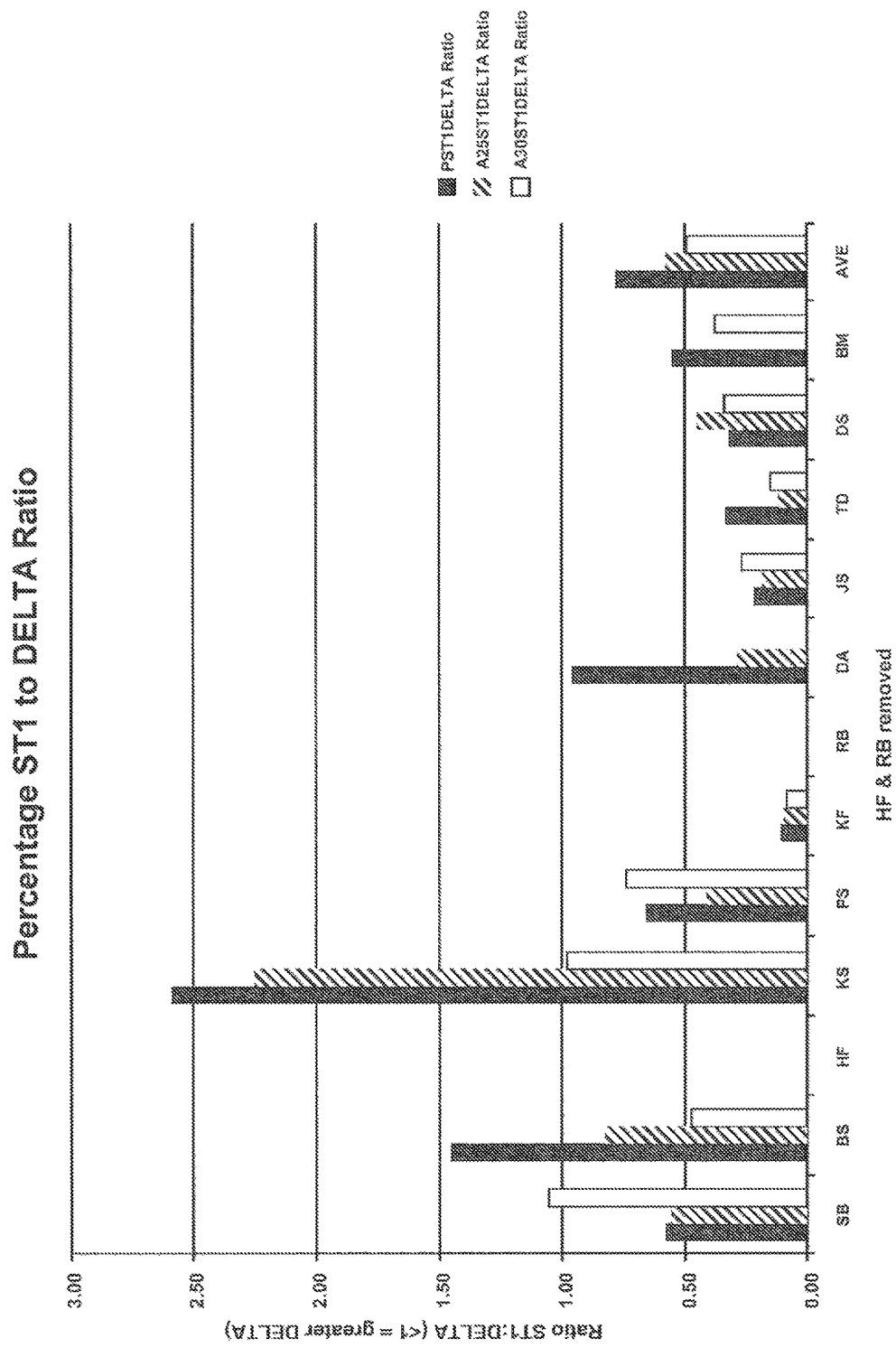
FIG. 1 is a bar graph of the ratio between stage 1 sleep percentage and DELTA sleep percentage for subjects who were administered placebo and the nutraceutical composition presented in Table 2.
Figure 2:
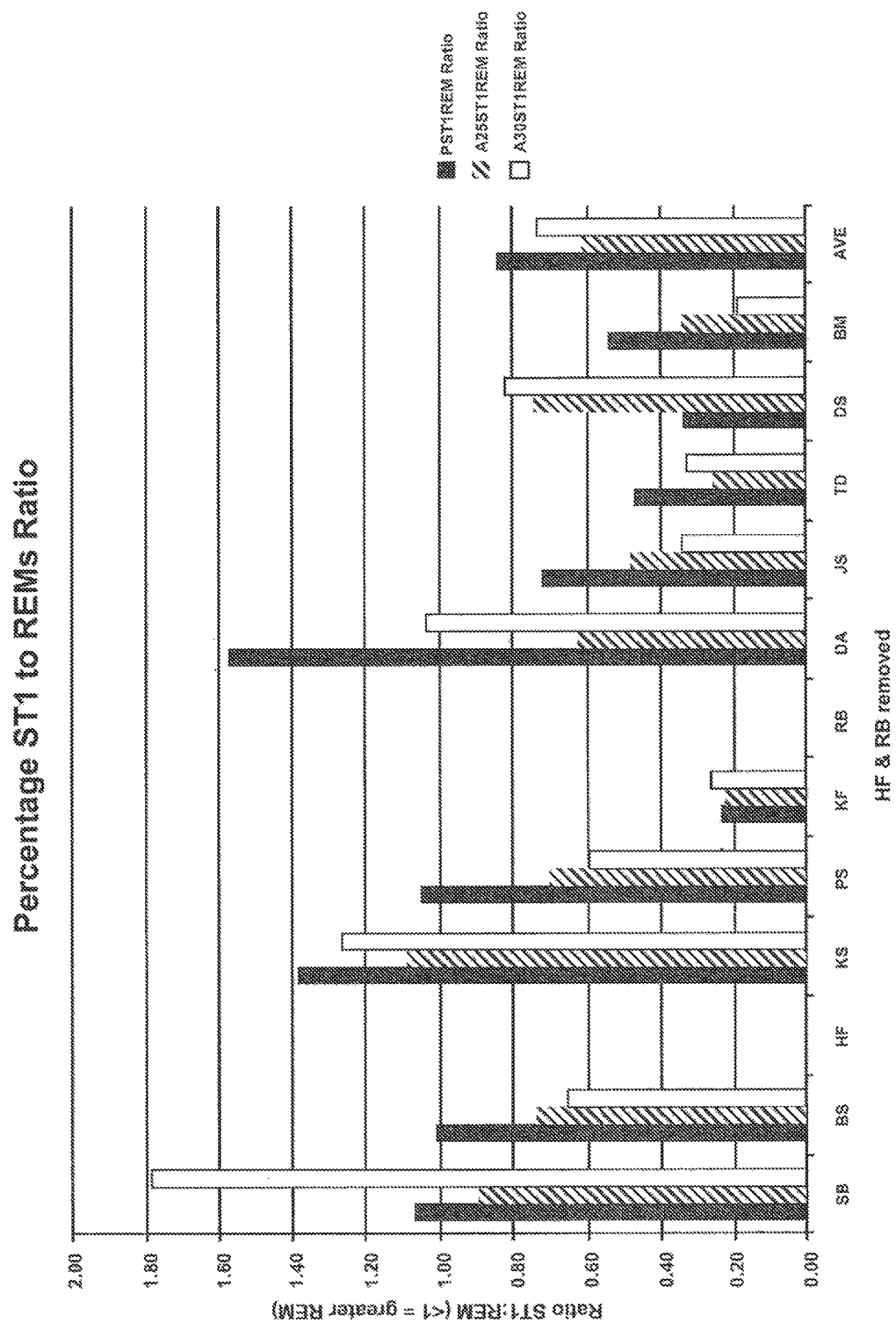
FIG. 2 is a bar graph of the ratio between stage 1 sleep percentage and REM sleep percentage for individuals who were administered placebo and the nutraceutical composition presented in Table 2.
Figure 3:
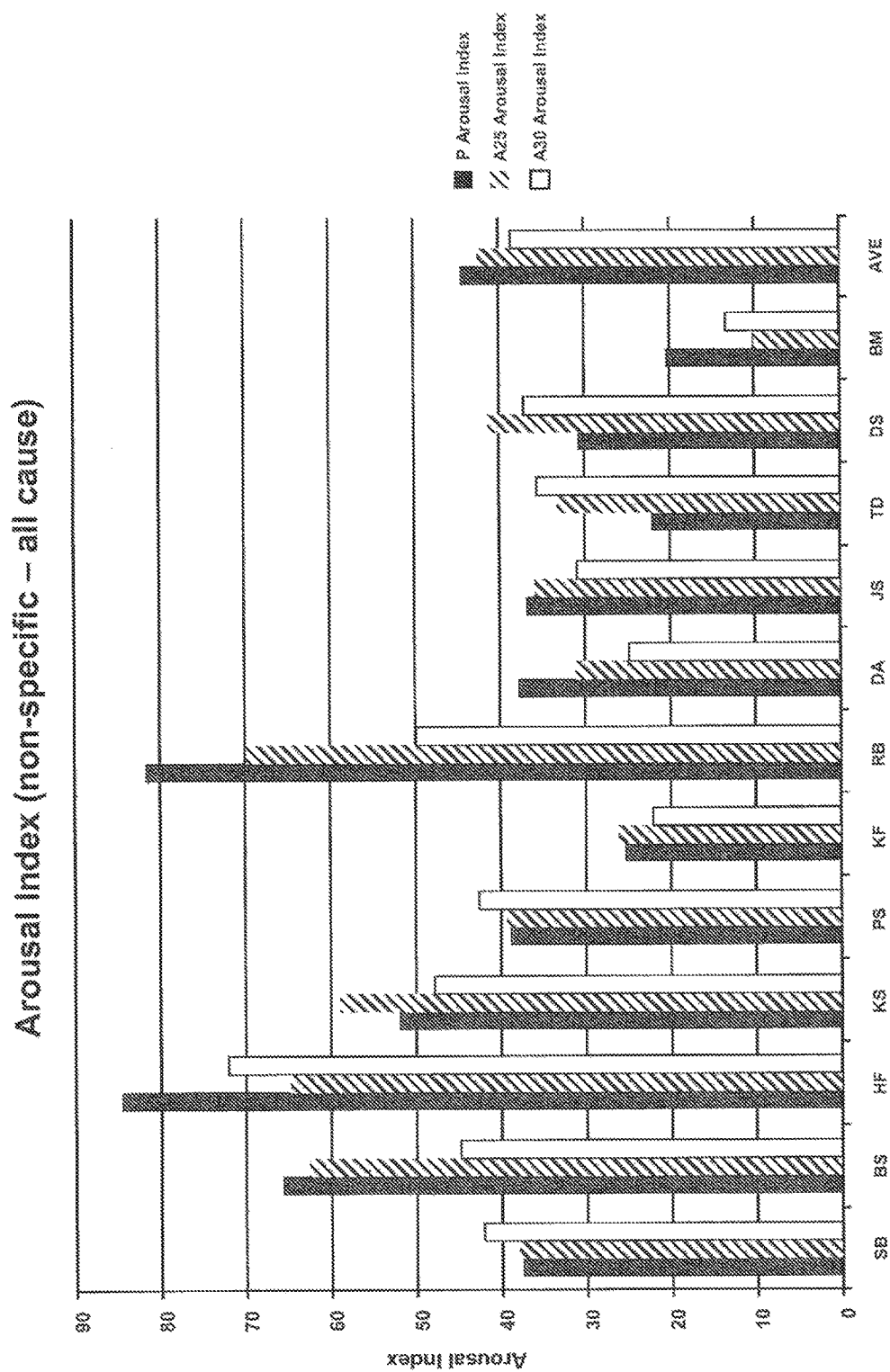
FIG. 3 is a bar graph of the all cause non-specific arousal indices of individuals who were administered placebo and the nutraceutical composition presented in Table 2.
Figure 4:
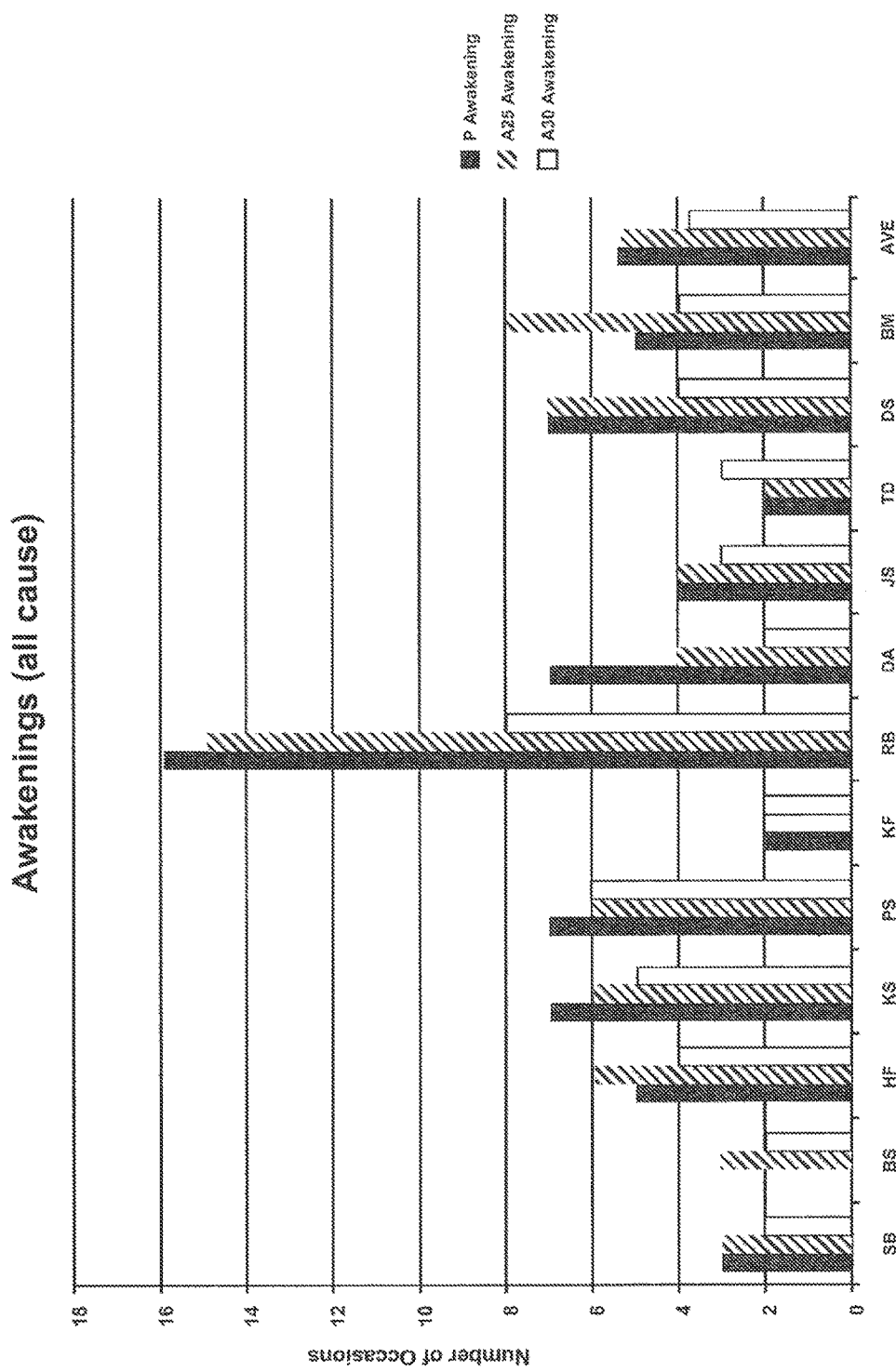
FIG. 4 is a bar graph of the awakenings of individuals who were administered placebo and the nutraceutical composition presented in Table 2.
Figure 5:
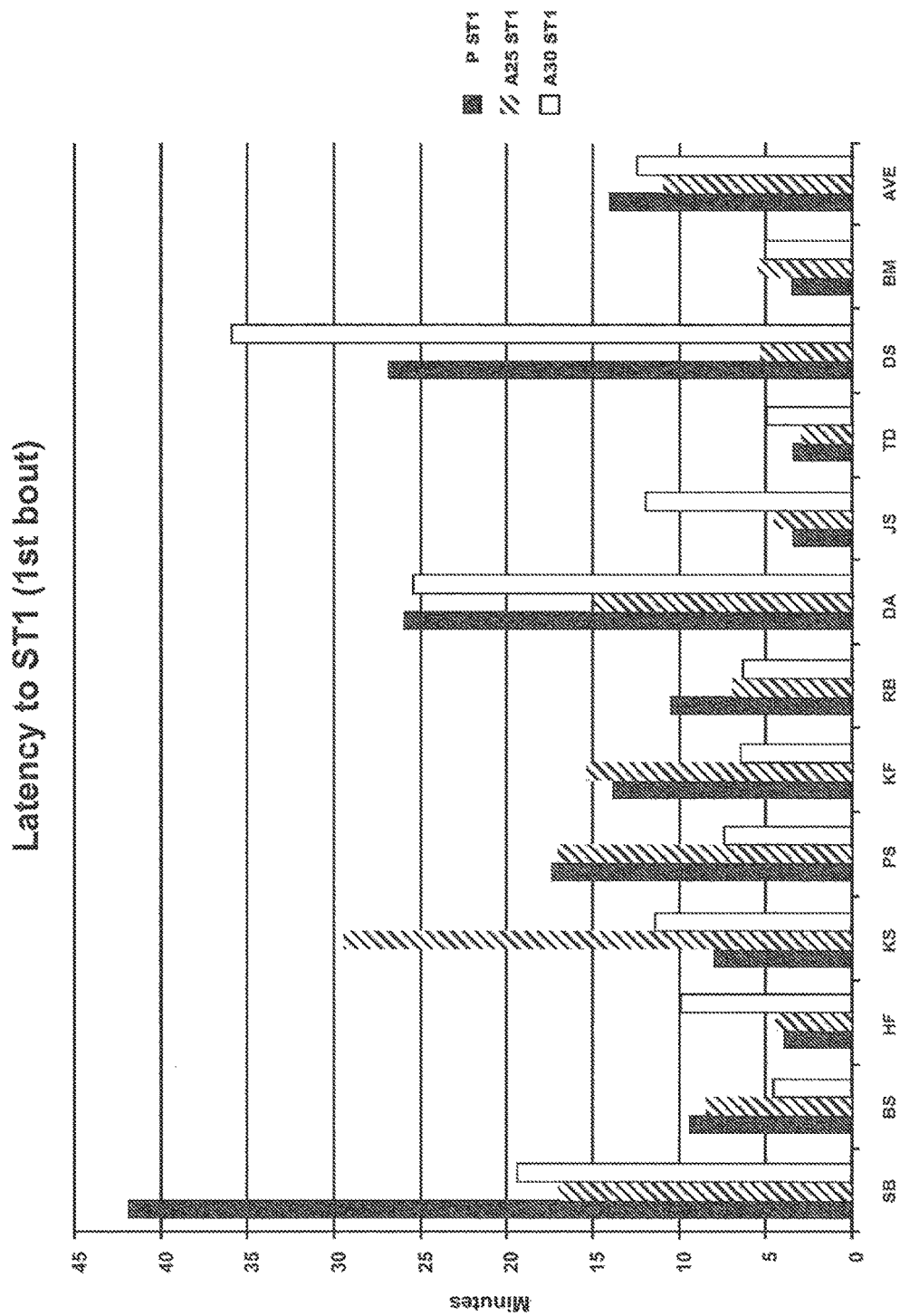
FIG. 5 is a bar graph of the latency to stage 1 sleep of individuals who were administered placebo and the nutraceutical composition presented in Table 2.
Figure 6:
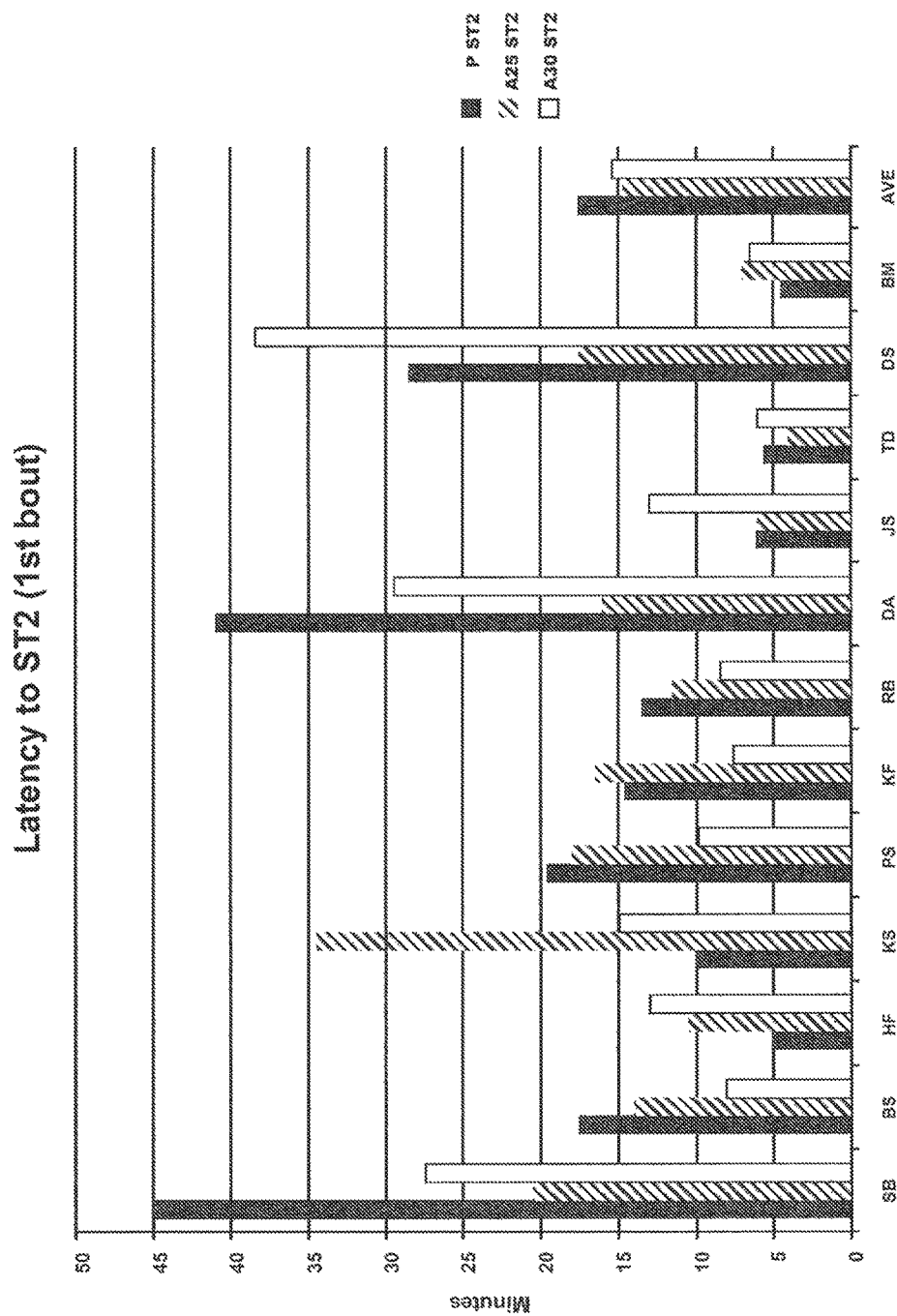
FIG. 6 is a bar graph of the latency to stage 2 sleep of individuals who were administered placebo and the nutraceutical composition presented in Table 2.
Figure 7:
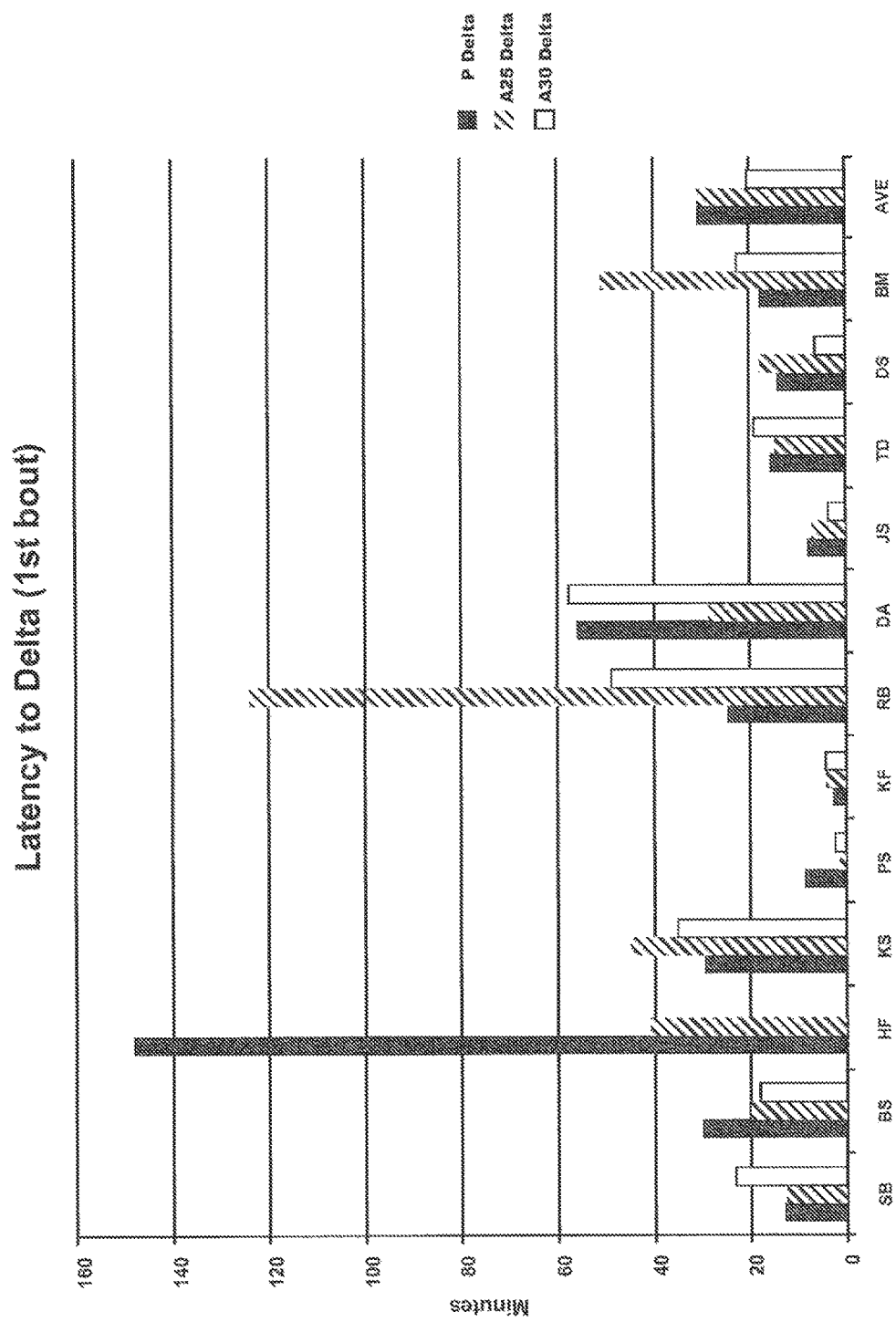
FIG. 7 is a bar graph of the latency to DELTA sleep of individuals who were administered placebo and the nutraceutical composition presented in Table 2.
Figure 8:
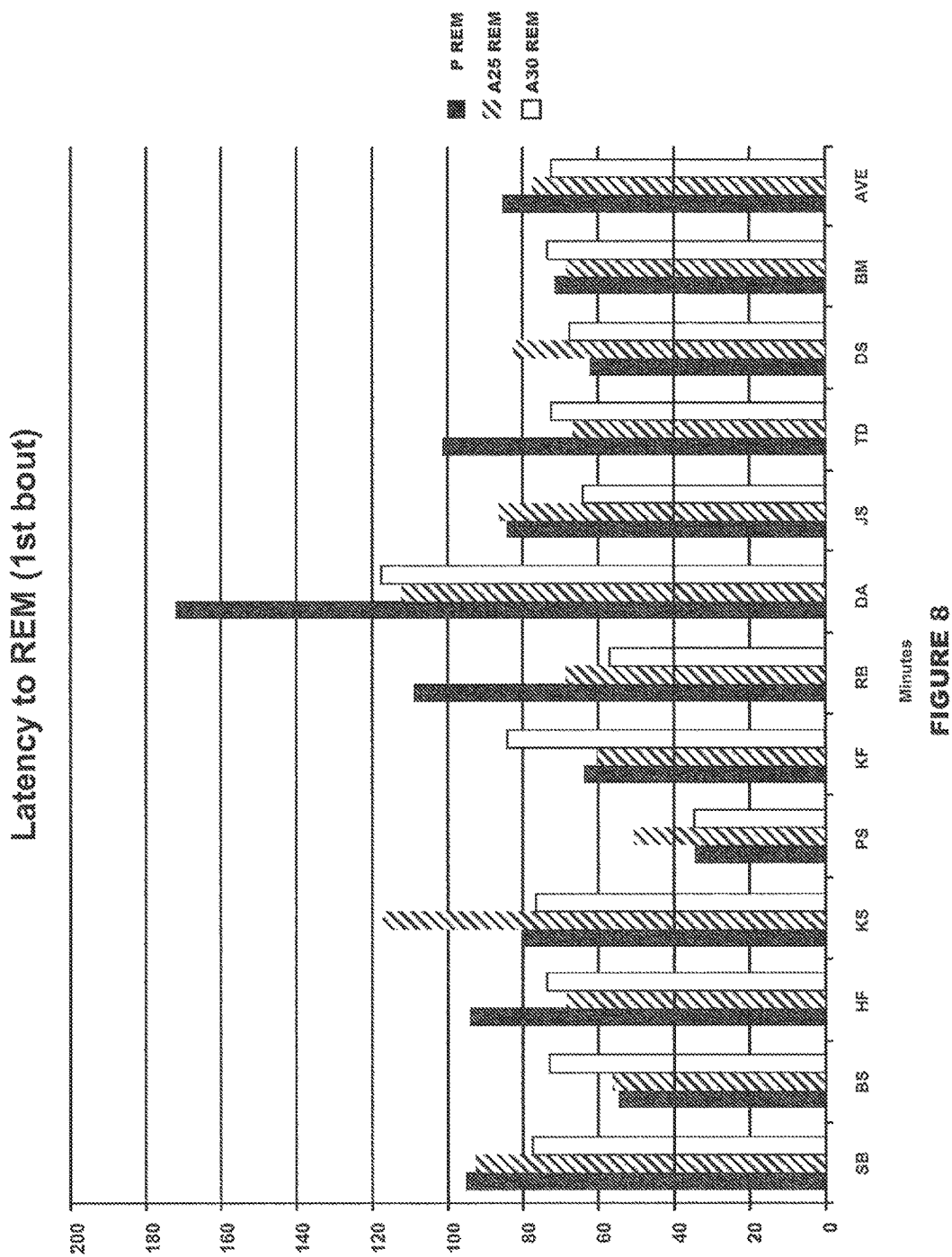
FIG. 8 is a bar graph of the latency to REM sleep of individuals who were administered placebo and the nutraceutical composition presented in Table 2.
Figure 9:
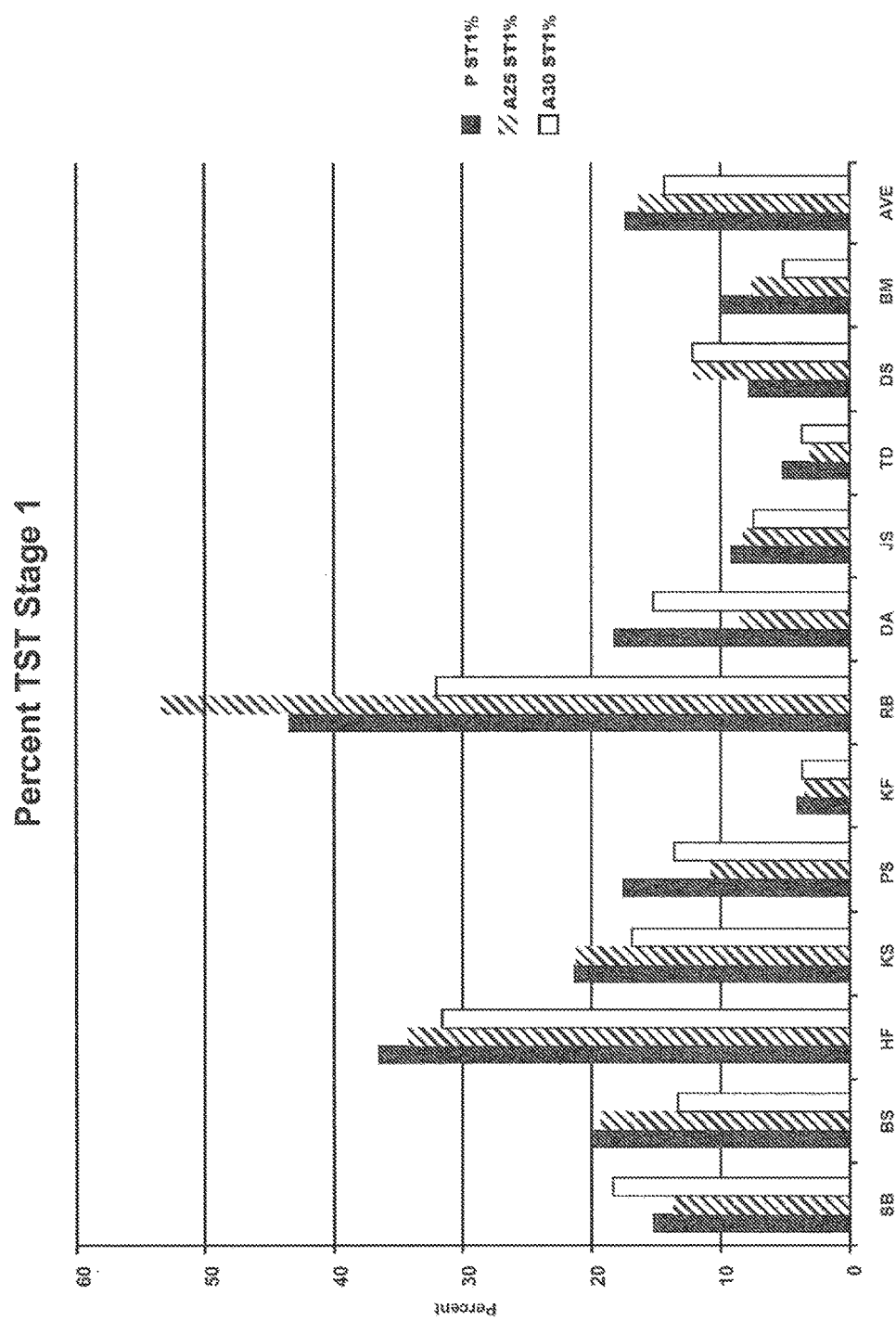
FIG. 9 is a bar graph of the percentage of total sleep time (TST) spent in stage sleep for individuals who were administered placebo and the nutraceutical composition presented in Table 2.
Figure 10:
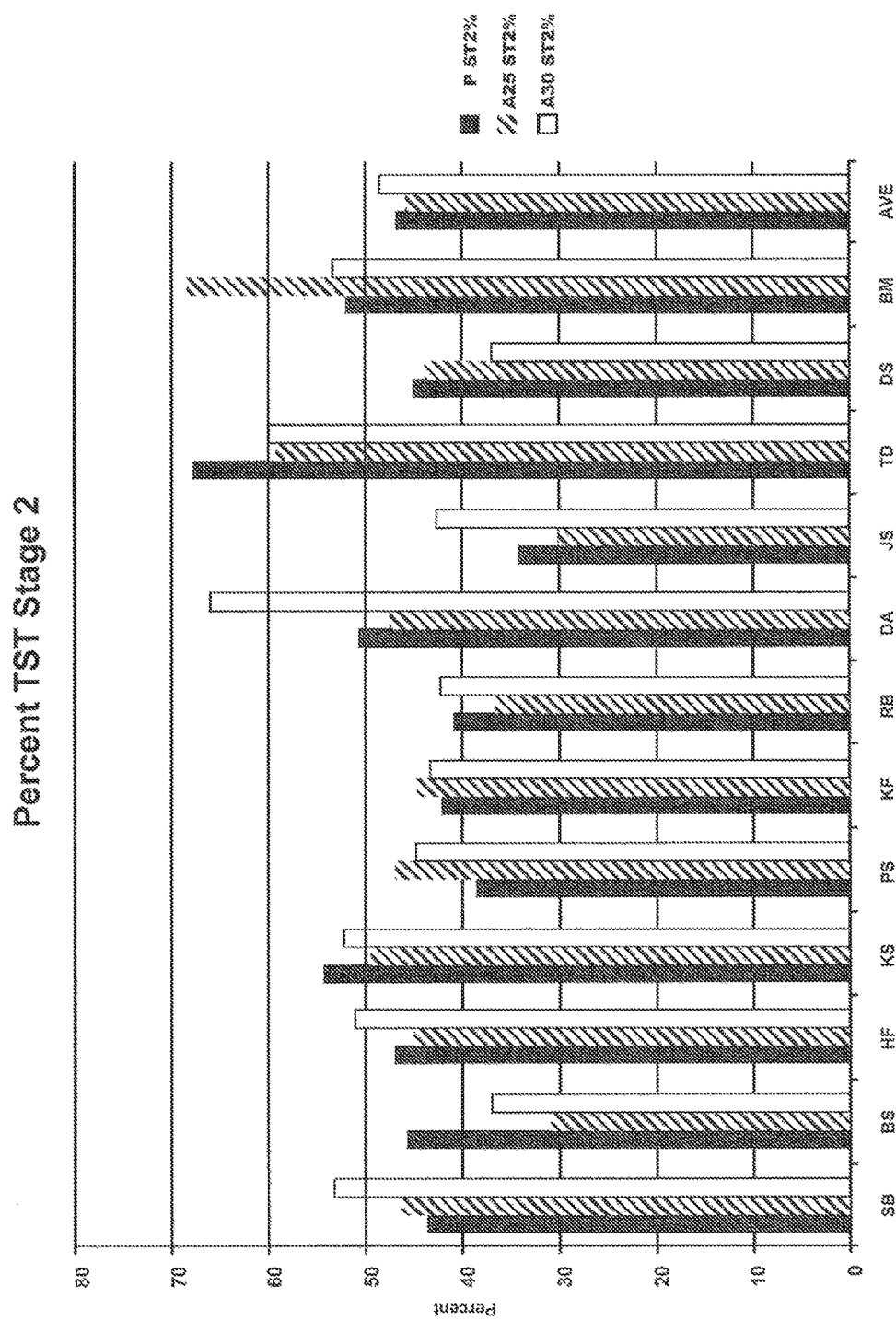
FIG. 10 is a bar graph of the percentage of total sleep time (TST) spent in stage 2 sleep for individuals who were administered placebo and the nutraceutical composition presented in Table 2.
Figure 11:
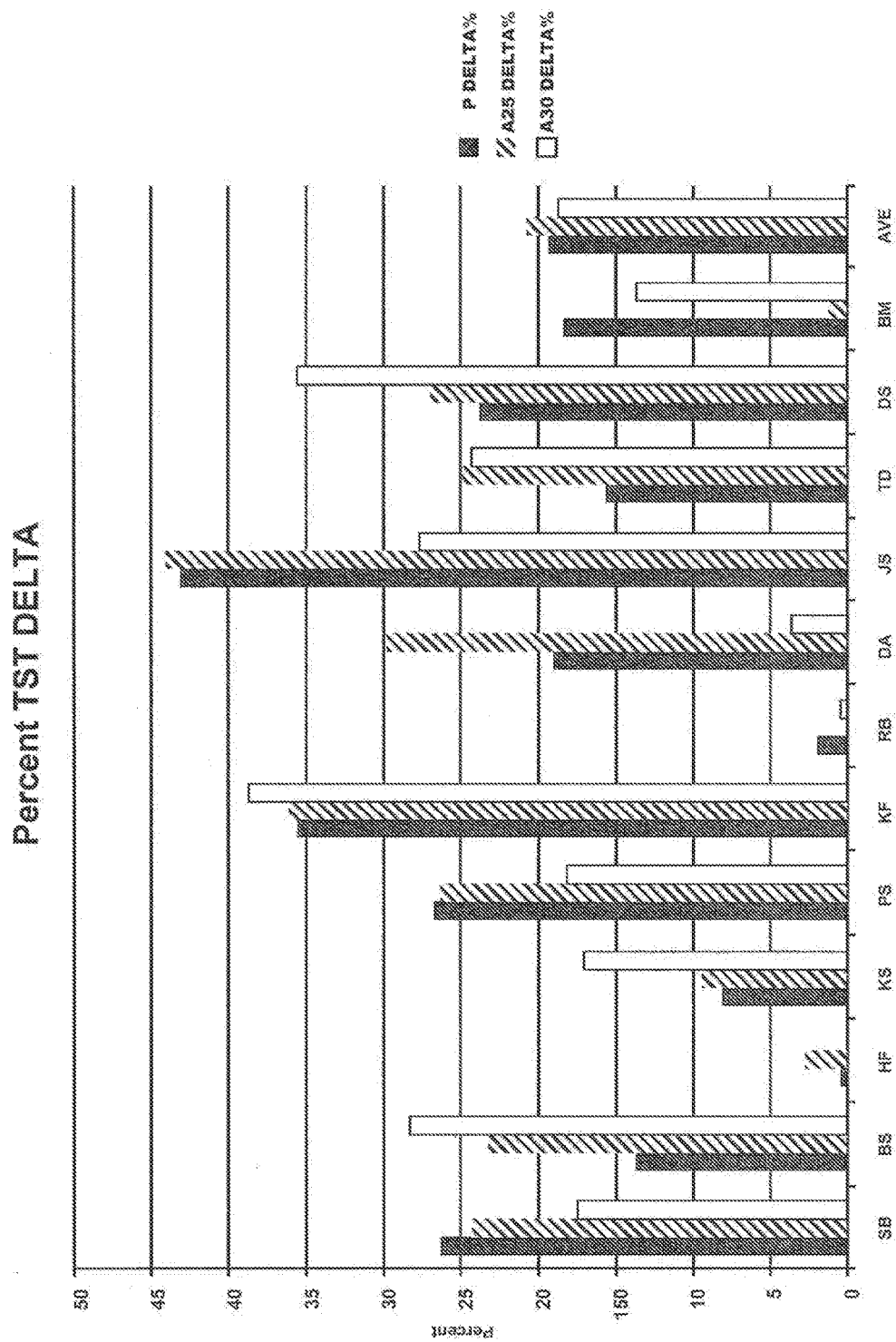
FIG. 11 is a bar graph of the percentage of total sleep time (TST) spent in DELTA sleep for individuals who were administered placebo and the nutraceutical composition presented in Table 2.
Figure 12:
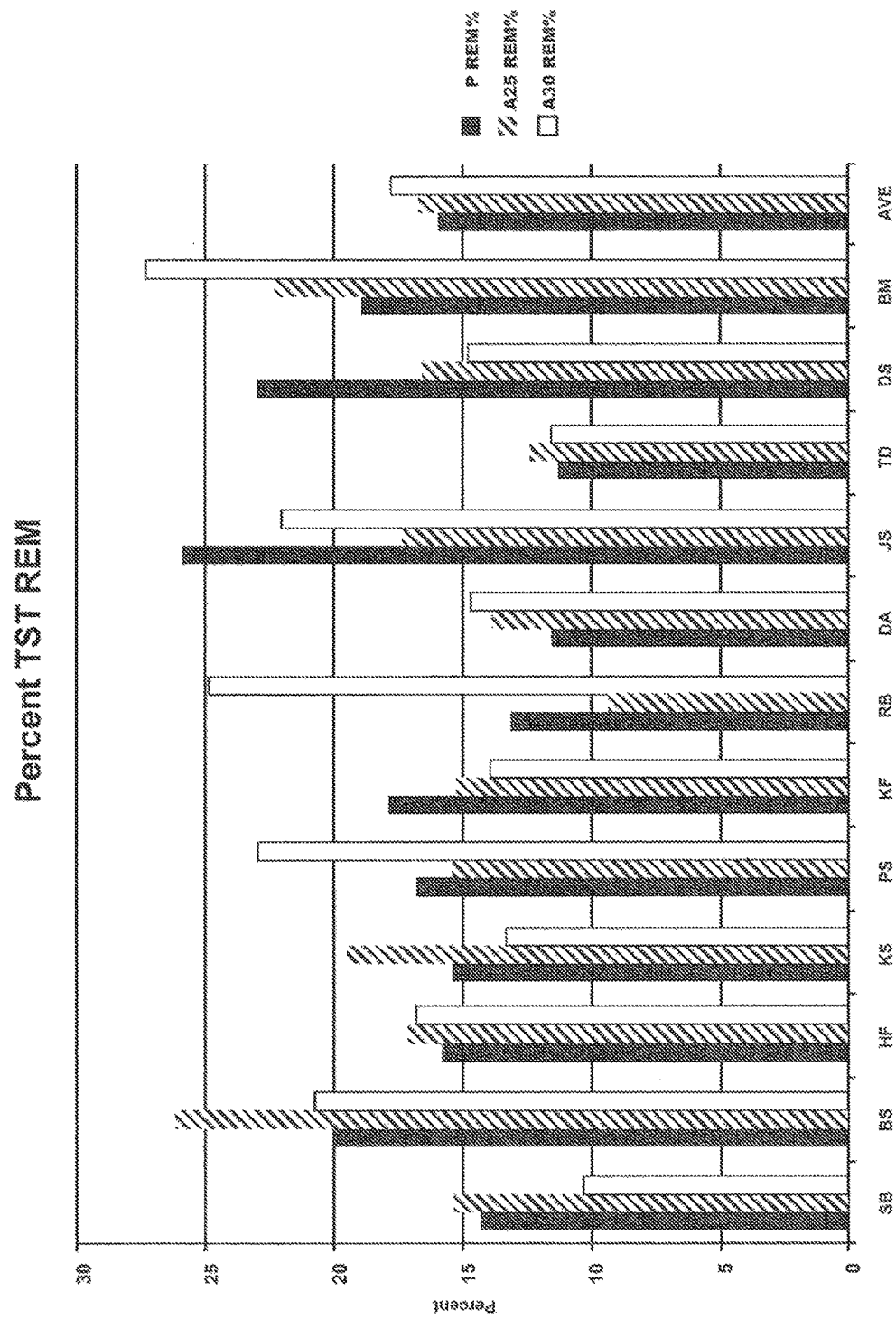
FIG. 12 is a bar graph of the percentage of total sleep time (TST) spent in REM sleep for individuals who were administered placebo and the nutraceutical composition presented in Table 2.
Figure 13:
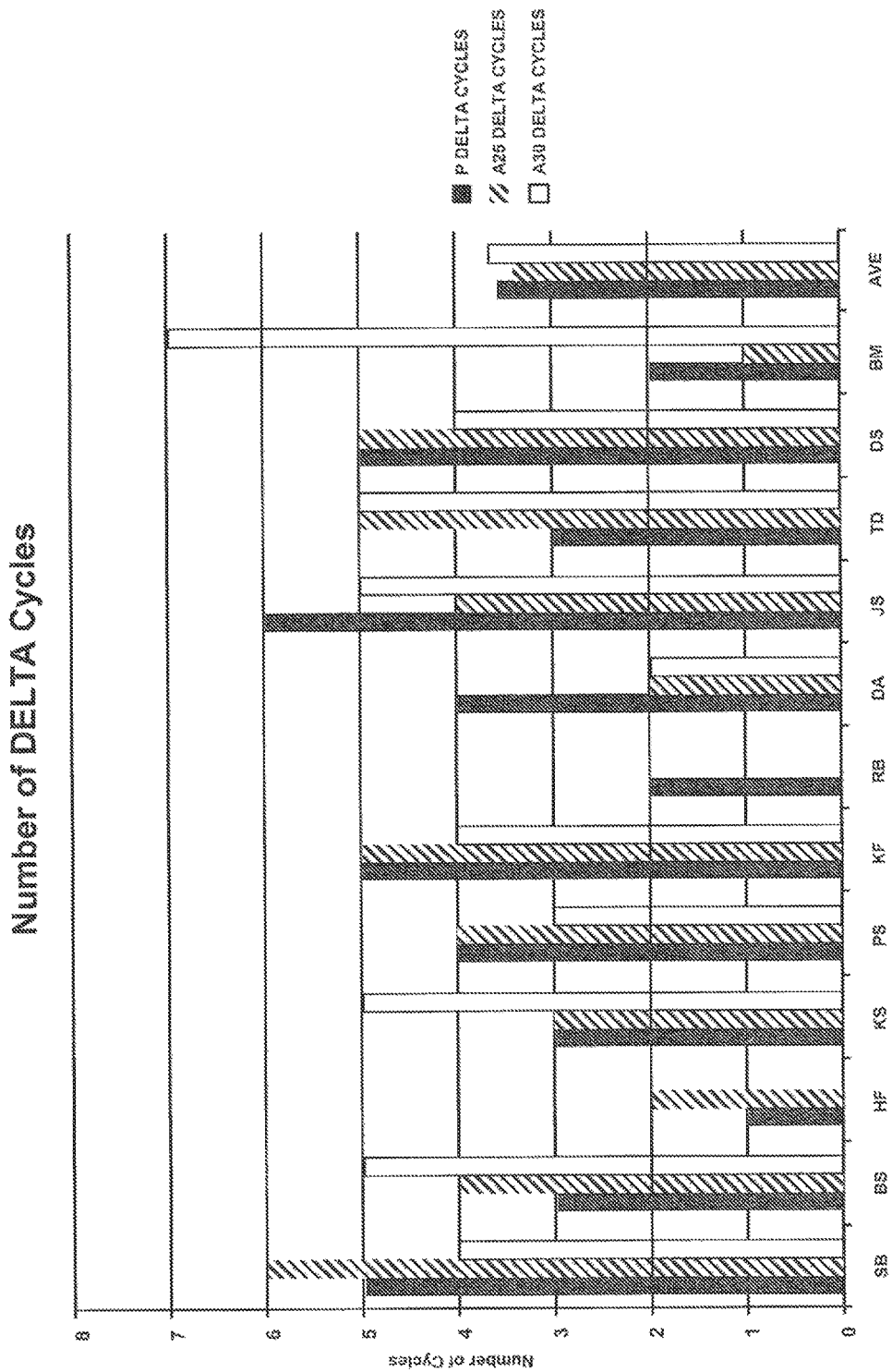
FIG. 13 is a bar graph of the number of DELTA sleep cycles for individuals who were administered placebo and the nutraceutical composition presented in Table 2.
Figure 14:
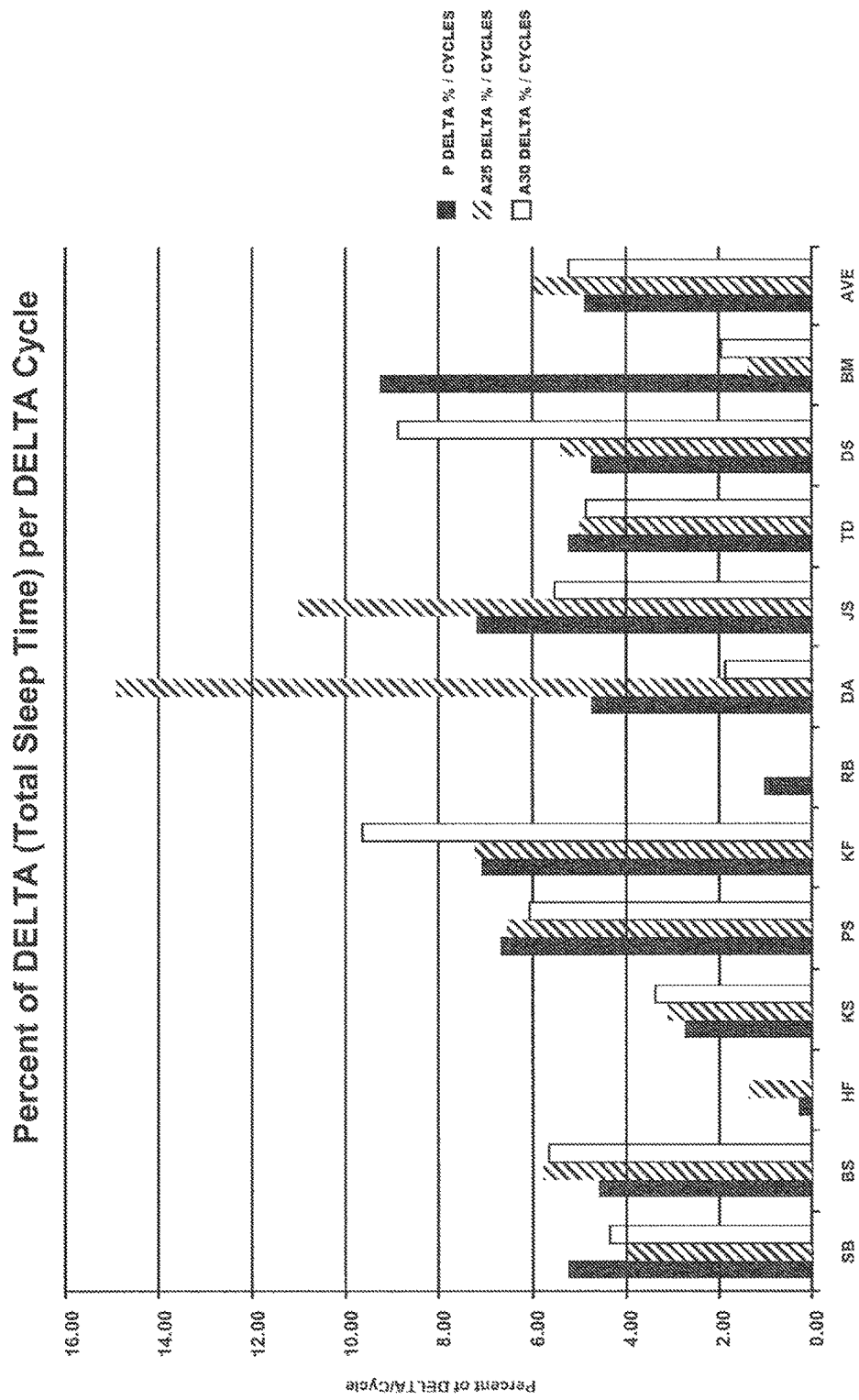
FIG. 14 is a bar graph of the percentage of DELTA sleep per DELTA cycle for individuals who were administered placebo and the nutraceutical composition presented in Table 2.
Figure 15:
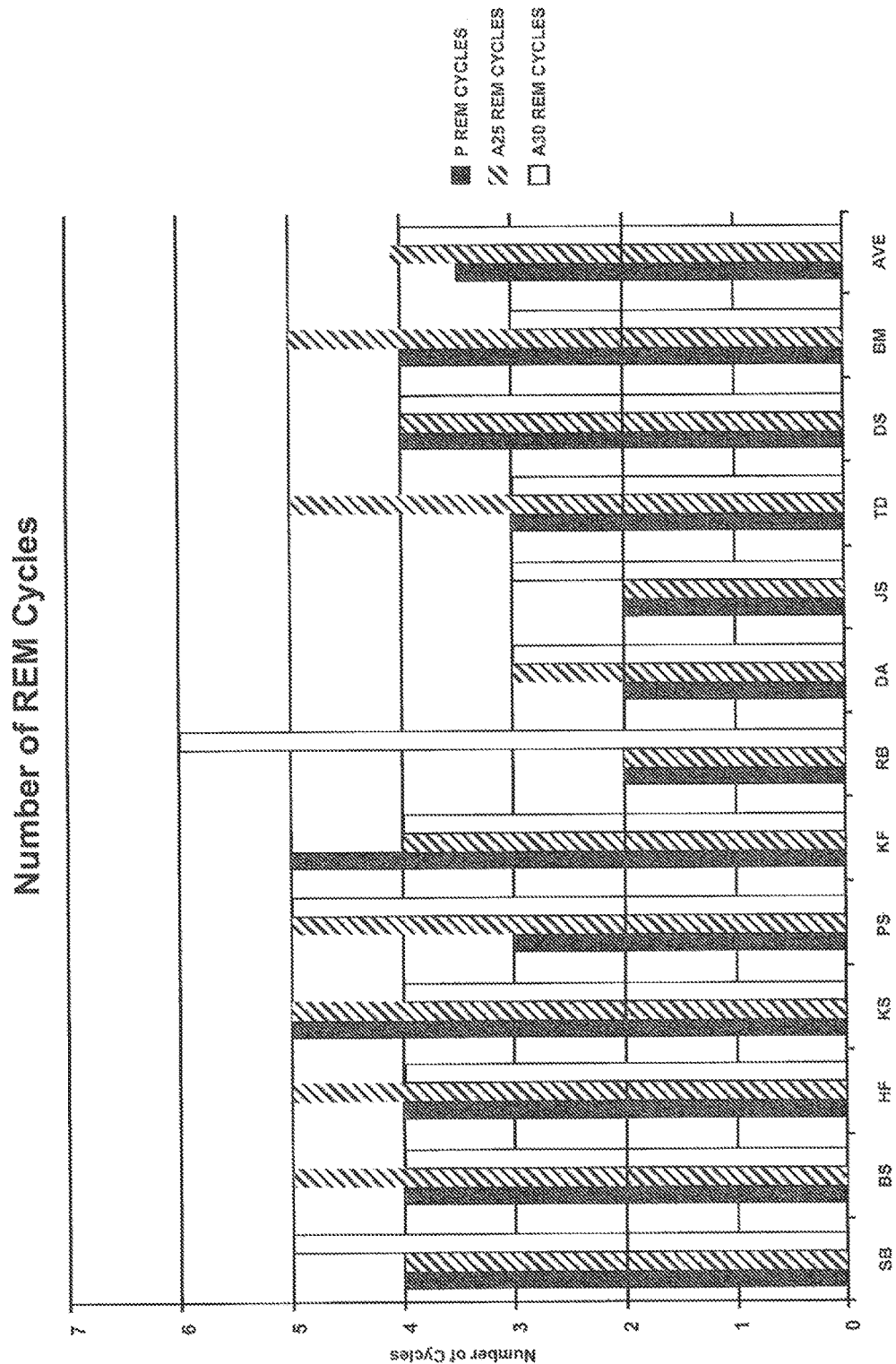
FIG. 15 is a bar graph of the number of REM sleep cycles for individuals who were administered placebo and the nutraceutical composition presented in Table 2.
Figure 16:
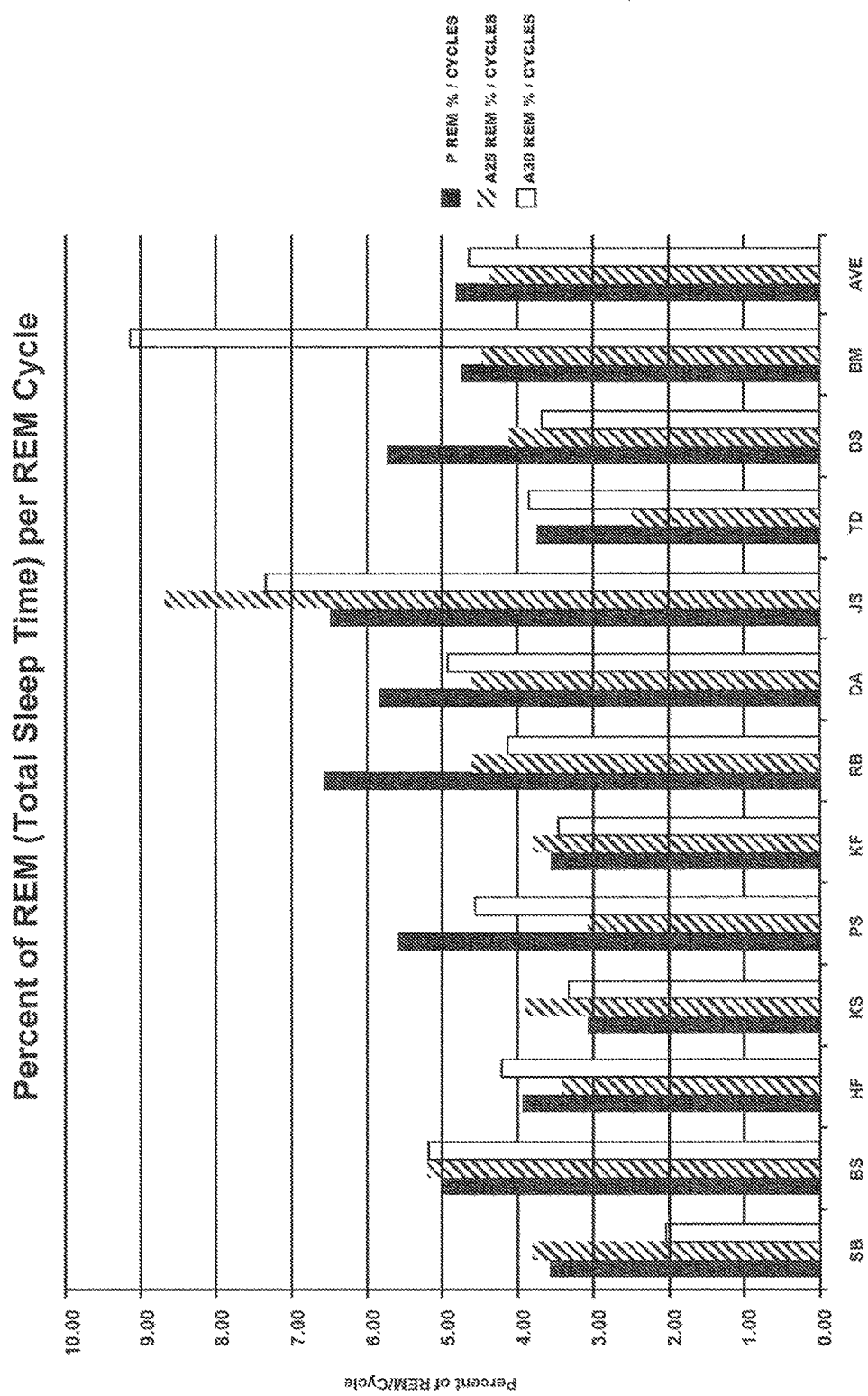
FIG. 16 is a bar graph of the percentage of REM sleep per REM cycle for individuals who were administered placebo and the nutraceutical composition presented in Table 2.
Figure 17:
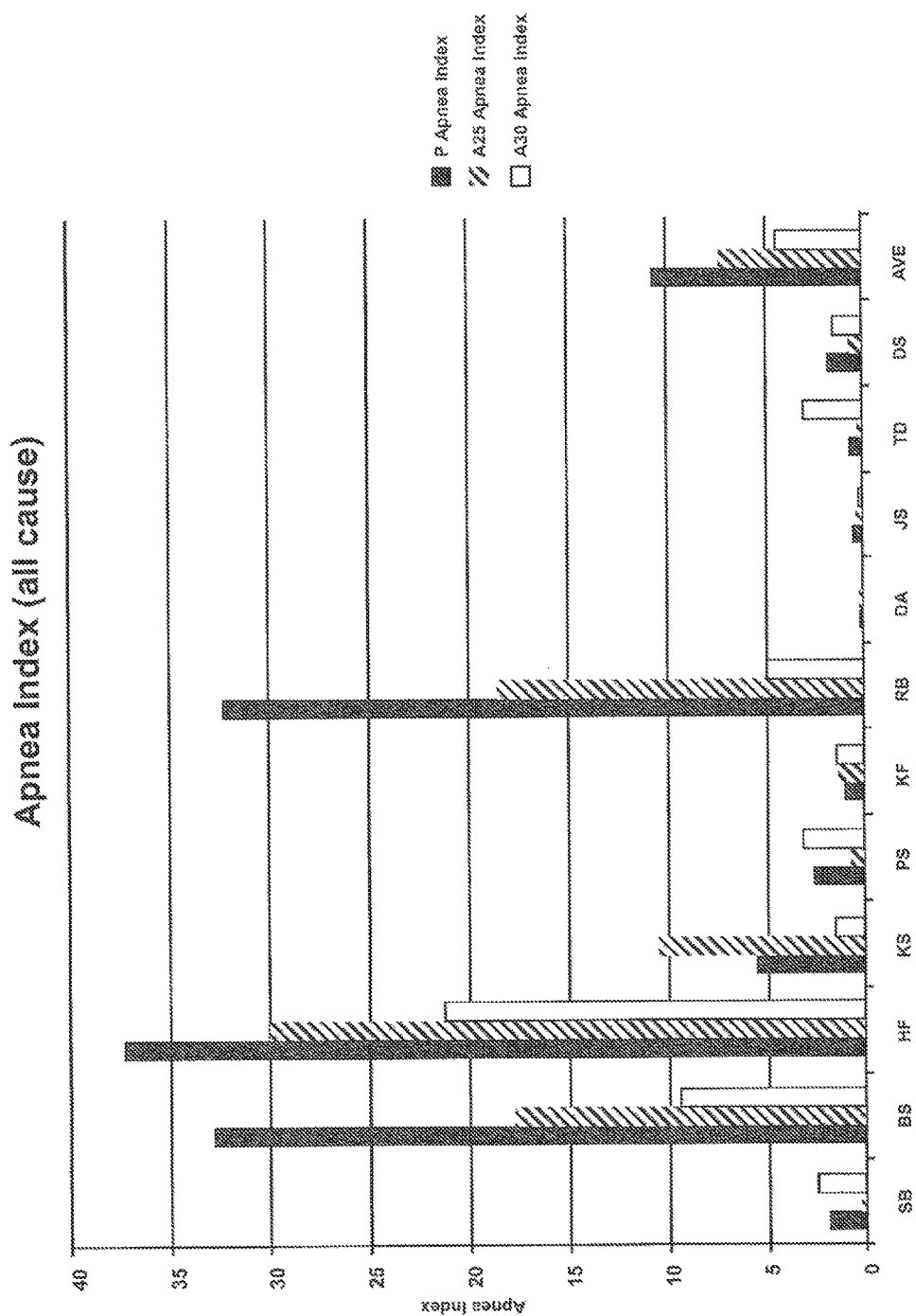
FIG. 17 is a bar graph of the apnea indices of individuals who were administered placebo and the nutraceutical composition presented in Table 2.
Figure 18:
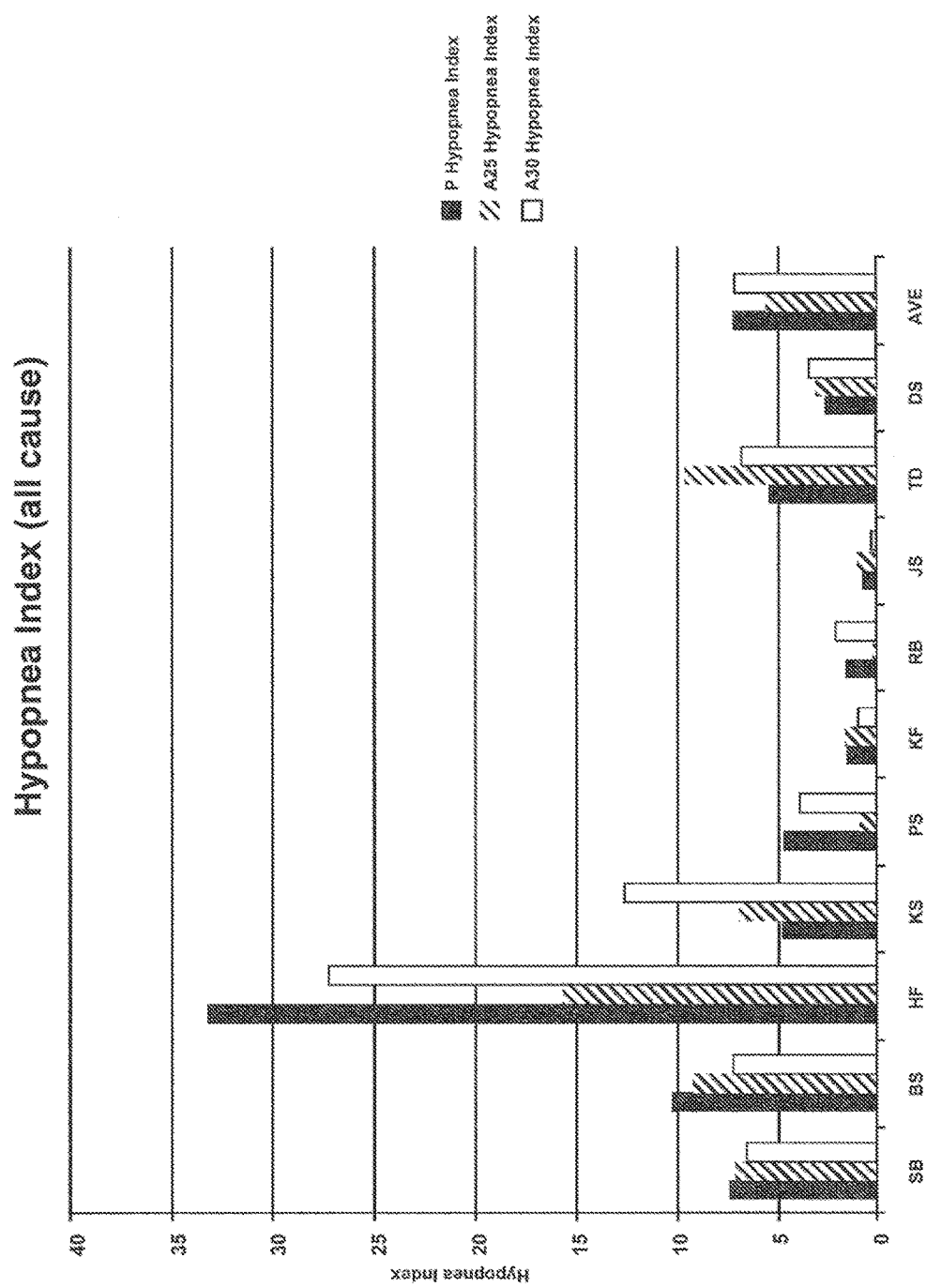
FIG. 18 is a bar graph of the hypopnea indices of individuals who were administered placebo and the nutraceutical composition presented in Table 2.
Figure 19:
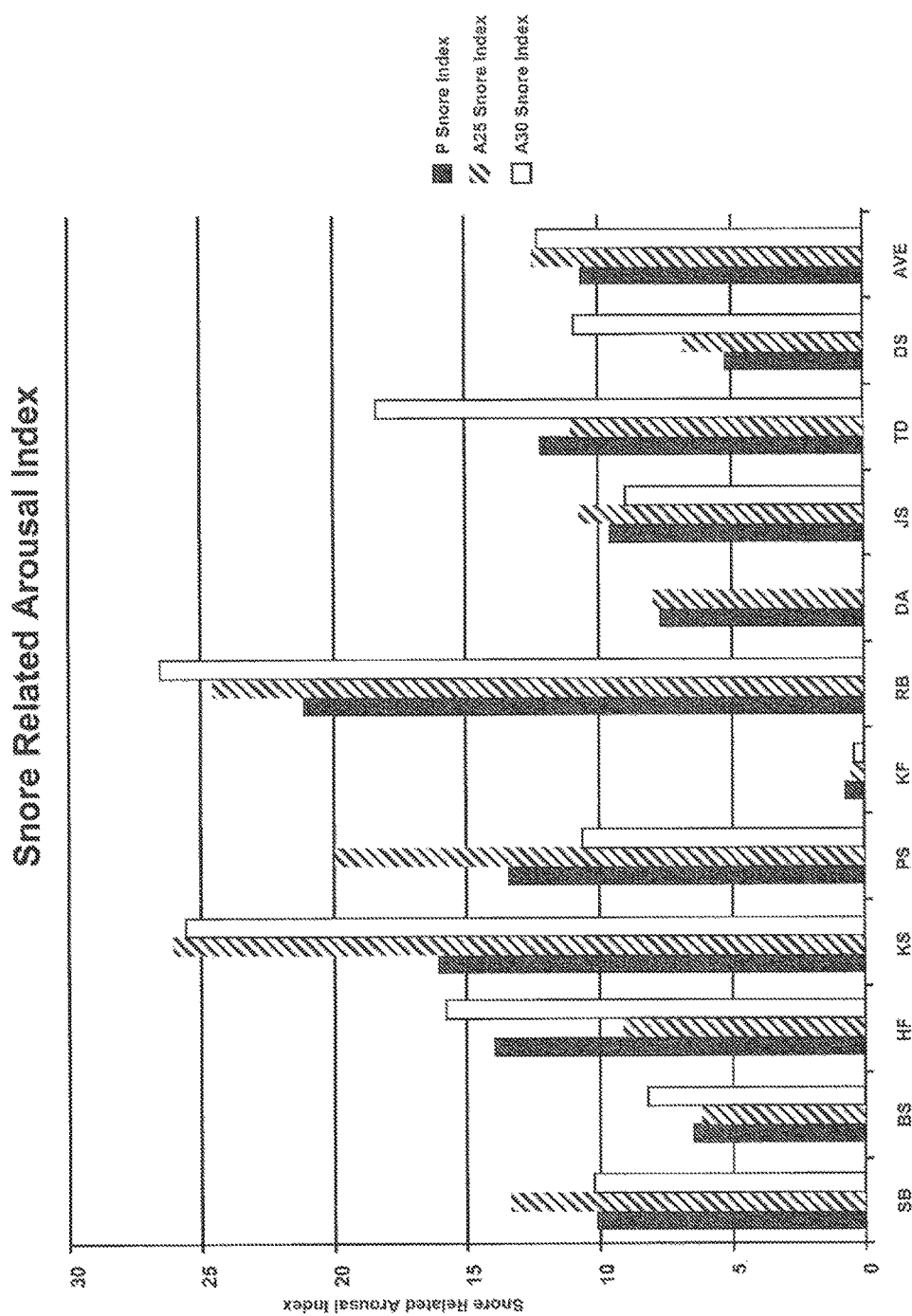
FIG. 19 is a bar graph of the snore related arousal indices of individuals who were administered placebo and the nutraceutical composition presented in Table 2.
Figure 20:
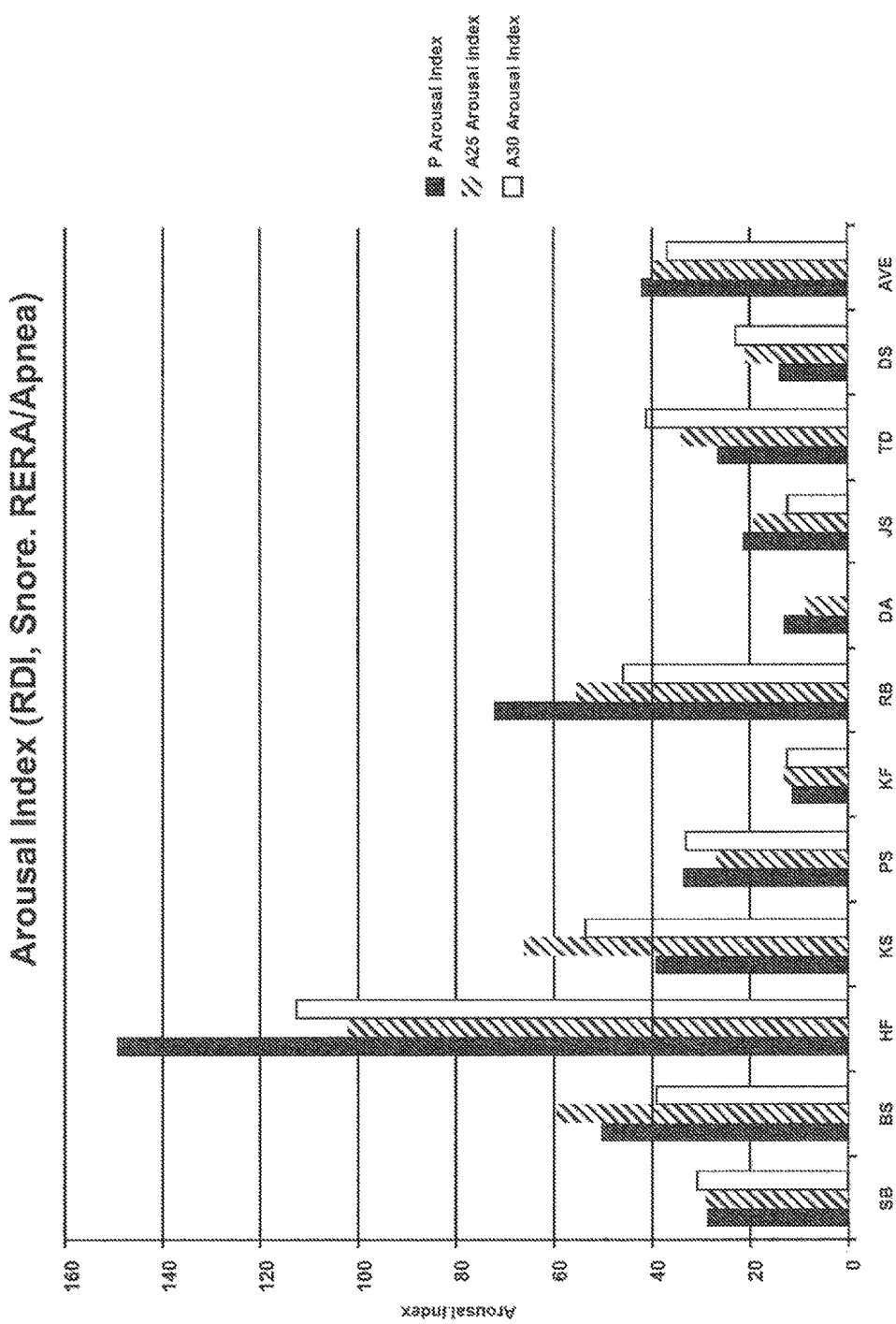
FIG. 20 is a bar graph of the arousal indices of individuals who were administered placebo and the nutraceutical composition presented in Table 2.

"Sleep" is defined generally herein as the body's rest cycle which is triggered by a complex group of hormones that respond to cues from the body itself and the environment. In response to these cues, an individual will begin to fall asleep and, normally, progress through a number of sleep stages (e.g., waking, non-rapid eye movement (e.g., non-REM or NREM) stages 1 to 4, and/or rapid eye movement (e.g., REM) sleep).

For example, sleep can be initiated by entering the "waking" sleep stage. The waking stage is referred to as relaxed wakefulness, because this is the stage in which the body prepares for sleep. All people fall asleep with tense muscles, their eyes moving erratically. Then, as a person becomes sleepier, the body begins to slow down. Muscles begin to relax, and eye roll movement slows.

Next, an individual can begin "non-rapid eye movement sleep" or "NREM sleep". About 80 percent of sleep is dreamless, NREM sleep. During NREM sleep, the breathing and heart rate are slow and regular, the blood pressure is low, and the sleeper is relatively still. NREM sleep is divided into four stages of increasing depth of sleep: Stage 1, Stage 2, and Stages 3 and 4. NREM sleep typically lasts from approximately 90 to 120 minutes, each stage lasting anywhere from 5 to 15 minutes. Stages 2 and 3 repeat backwards before rapid eye movement (REM) sleep is attained. Therefore, a normal sleep cycle has the following pattern: waking, stage 1, 2, 3, 4, 3, 2, REM. Usually, REM sleep occurs approximately 90 minutes after sleep onset.

"Latency" is defined herein as the amount of time required for an individual to enter a sleep stage. "Stage I latency" is defined herein as the time in minutes from when an individual begins attempting to fall asleep until the onset of the first bout of Stage 1 sleep. "Stage 2 latency" is defined herein as the time in minutes from sleep onset to the onset of the first bout of Stage 2 sleep. "Stage 3/4 latency" or "DELTA latency" is defined herein as the time in minutes from sleep onset to the onset of the first bout of Stage 3/4 sleep. "REM Latency" is defined herein as the time in minutes from sleep onset to the onset of the first bout of REM sleep.

It is also important to note that sleep stages are not necessarily sequential. For instance, if a person is exhausted he or she may skip Stages 1 and 2 and move directly into Delta or REM. Most adults utilize approximately eight hours of sleep on a regular schedule to function well, although some require less, and others more. Children, particularly teenagers, often need nine or ten hours for optimal functioning.

"Stage 1" sleep, or drowsiness, is often described as first in the sequence, especially in models where waking is not included. Polysomnography (PSG) can show a 50% reduction in activity between wakefulness and stage 1 sleep. The eyes are closed during Stage 1 sleep, but if aroused from it, a person may feel as if he or she has not slept. Stage 1 may last for approximately 5 to 10 minutes.

"Stage 2" sleep is a period of light sleep during which PSG readings can show intermittent peaks and valleys, or positive and negative waves. These waves indicate spontaneous periods of muscle tone mixed with periods of muscle relaxation. Muscle tone of this kind can be seen in other stages of sleep as a reaction to auditory stimuli. The heart rate slows, and body temperature decreases. At this point, the body prepares to enter "deep sleep" stages.

"Stages 3 and 4" or "DELTA" or NREM sleep are deep sleep stages. These stages are known as slow-wave sleep. During slow-wave sleep, the electromyogram records can show waves of high amplitude, indicating a pattern of deep sleep and rhythmic continuity.

"Rapid Eye Movement" or "REM" is a normal stage of sleep characterized by the rapid movement of the eyes. Criteria for REM sleep can include, for example, rapid eye movement, low muscle tone and a rapid, low voltage EEG. REM sleep in adult humans typically occupies approximately 20% to 25% of total sleep, about 90 to 120 minutes of a night's sleep. During a normal night of sleep, humans usually experience about four or five periods of REM sleep; they are quite short at the beginning of the night and longer toward the end. During REM, the activity of the brain's neurons is quite similar to that during waking hours; for this reason, the sleep stage may be called paradoxical sleep. This means that there are no dominating brain waves during REM sleep. Vividly recalled dreams mostly occur during REM sleep.

"Sleep Efficiency" is defined herein as a percentage that reflects the percentage of time asleep versus the total time in bed. E.g., total sleep time (TST)=386 minutes; Sleep period total/time in bed=424 minutes; Sleep Efficiency=89.1%.

"Stage specific % of TST" is the percentage of TST of any given stage (accumulated) E.g., TST=386 minutes; total time in REM=48 minutes; REM % TST=12.4%.

The "Percentage of Stage I to DELTA" or "Percentage of Stage 1 to REM" is defined herein as a percentage of the time spent in Stage I sleep relative to the amount of time spent in DELTA or REM sleep. Since DELTA and REM are restorative sleep stages that are often limited in disordered sleep, a decrease of the amount of Stage I sleep relative to DELTA and/or REM sleep is considered beneficial, by at least those familiar with the field of sleep study.

Sleep studies are often performed to access an individuals' overall quality of sleep and/or to diagnose any sleep disorders that may be present. The data during a sleep study is analyzed in 30 second windows termed "epochs". The staging of sleep is determined by the predominate features of each epoch. Any interruption in staged sleep greater than 60 seconds (2 epochs) is considered an "awakening".

"About" when used with a stated numeral value is intended to mean a variance of ±5% from the stated numerical value.

"Arousals" occur regularly during sleep. Each time one shifts from one stage of sleep to another there is a momentary interruption of sleep or an arousal. If an arousal continues for greater than 60 seconds (2 epochs) it is then generally deemed an awakening.

The "Arousal Index" is defined herein as the total number of Arousals divided by the total number of sleep in hours or total sleep time. E.g., TST=6.43; Total number of arousals=388 Arousal Index=54.9 or 54.9 arousals per hour.

Sleep studies are often used to diagnose and/or confirm suspected sleep disorders such as, but not limited to, "sleep apnea". "Apnea" literally means "without breath." There are three types of apnea: obstructive, central, and mixed. Of the three types of apnea, obstructive is the most common. The root cause of each type of apnea is distinct but, in all three, individuals stop breathing repeatedly during their sleep. This can occur hundreds of times during the night and often for a minute or longer. "Obstructive sleep apnea" or "OSA" is caused by a blockage of the airway, usually when the soft tissue in the rear of the throat collapses and closes during sleep. In "central sleep apnea", the airway is not blocked but the brain fails to signal the muscles to breathe. "Mixed apnea", as the name implies, is a combination of obstructive and central sleep apnea. With each apnea event, the brain briefly arouses people with sleep apnea in order for them to resume breathing, but consequently sleep is extremely fragmented and of poor quality.

The "Apnea Index" is the total number of incidents of sleep apnea divided by the total number of minutes of sleep.

Sleep apnea may result in lowered oxygen saturation levels in the blood of affected individuals. "Hypoxic time" is the total time in minutes that the oxygen saturation levels in the blood are below 89.0% E.g., SaO2 of <89: 0.0 minutes indicates that the blood oxygen saturation levels did not fall below zero during the duration of sleep analyzed.

"Nap" or "short duration sleep" is typically defined as a short sleep especially during the day. "Short duration sleep" and/or "nap" are defined herein, as a period of sleep lasting one hour or less.

"Polysomnography" or "PSG", also known as a sleep study, is defined herein as a multi-parametric test used in the study of sleep and as a diagnostic tool in sleep medicine. The test result is called a "polysomnogram", also abbreviated "PSG". Polysomnography, as defined herein, is a comprehensive recording of the biophysiological changes that occur during sleep. It is usually performed at night, when most people sleep. The PSG monitors many body functions including brain (EEG), eye movements (EOG), muscle activity or skeletal muscle activation (EMG) and heart rhythm (ECG) during sleep. After the identification of the sleep disorder sleep apnea in the 1970s, the breathing functions respiratory airflow and respiratory effort indicators were added along with peripheral pulse oximetry. Additional details related to performing a PSG and the results of such study are contemplated and included herein as being known to practitioner's having ordinary skill in the sleep study art.

"Enhanced sleep quality" is defined herein as a period of sleep characterized by decreased ratio of stage 1 sleep to DELTA sleep, decreased ratio of stage 1 sleep to REM sleep, decreased number of awakenings, decreased number of arousals, decreased latencies, increased levels of blood oxygen saturation, decreased number of sleep disorder events such as, but not limited to, apneaic events, and/or any other outcome that would be recognized as enhancing sleep quality by one of ordinary skill in the field of sleep studies.

"Ultra-low dose" is defined herein as being a dose having micro- and/or nano-quantities of active constituents in a carrier.

"Micro-quantity" is defined herein as a quantity of about $^{-6}$ or less, but not being a nano-quantity.

"Nano-quantity" is defined as a quantity of about $^{-9}$ or less.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

Nutraceutical/Supplement Compositions/Formulations for Enhanced Sleep Quality

It has been unexpectedly and surprisingly discovered that the dose of a vitamin, mineral, or other nutritional ingredient when formulated into one or more compositions of the present invention and adapted for delivery via a system that substantially avoids first pass metabolism, may be significantly reduced while still producing a desired beneficial effect/biological response (e.g., increased sleep duration, decreased latency, etc.). As a result, the ingredients of one or more nutraceutical compositions and/or formulations of the present invention may be provided at substantially lower levels (i.e. ultra-low levels) than conventional amounts (e.g., RDA, UL, UDA, etc.). Furthermore, it has been surprisingly discovered that such ultra-low dosage levels and bioactive delivery systems allow the compositions/formulations of the present invention to be repeatedly and flexibly administered to an animal or human for the enhancement and augmentation of those biological functions (e.g., stages of sleep) known to be influenced by any of the individual components.

Without wanting to be bound by any particular theory, it is believed that administration of the ultra-low dose nutraceuticals of the present invention results in the initiation of signaling pathways (negative and/or positive feedback regulatory processes) and/or cascades that induce desired biological responses including, but not limited to, enhanced sleep quality.

For example, it is believed that due to the ultra-low dosage levels utilized in the present invention, a specific composition may be taken by an individual multiple times within each dosing period (e.g., within each 24 hour, 6 hour, or 1 hour period). Alternatively, an individual may take multiple, different compositions or formulations of the present invention within a dosing period to generate varied biological responses or effects, namely those associated with sleep disorders or the different stages of sleep. Thus, the presently described technology may be utilized in a system which allows an individual to biologically configure their dietary supplement intake throughout a dosing period or multiple dosing periods, based on their individual sleep needs or disorder(s).

Accordingly, the presently described technology provides for one or more ultra-low dose nutraceutical compositions or formulations comprising vitamins, minerals, enzymes, amino acids, adjuncts, and additives that can be administered to enhance sleep quality or treat sleep disorders.

Below is a detailed description of some of the components in the presently described ultra-low dose nutraceutical formulations/compositions of the present invention, their delivery systems for administration, and the sleep-based biological effects elicited thereby.

Water

The water can vary from source to source, but preferably contains at least calcium and magnesium in the amounts disclosed herein (below). Most preferably, the presently described technology utilizes water from an Appalachia water source, preferably a water source from the Eastern slope of the Shenandoah Valley. Different water sources would require empirical analysis of its constituents to ensure that the dosage amounts are consistent with spirit of the presently described technology.

The water is preferably filtered to purify and refine it from the certain, selected water-source. An example of components that the water can include, and tolerances for the amounts of those components, is set forth below:

Calcium: 0 mg/L to about 12.4 mg/L±25%;
Chromium: 0 mg/L to about 0.001 mg/L±25%;
Magnesium: 0 mg/L to about 5.8 mg/L±25%;
Manganese: 0 mg/L to about 0.001 mg/L±25%;
Potassium: 0 mg/L to about 1.4 mg/L±25%;
Sodium: 0 mg/L to about 1.6 mg/L±25%;

In an additional embodiment, the water may contain from 0 to 0.10 milligrams/Liter±25% of at least one nitrate and from 0 to 0.10 milligrams/Liter (+) 25% of at least one nitrite.

Any of these preferred components of the water may range from 0 to about ±25%. The pH of the water can range from about 5 to about 7.5. Preferably, the pH of the water is about 7.50 at 25 degrees Celsius.

In at least one embodiment, a nutraceutical composition of the present invention contains water in the volume of from about 0.15 milliliters to about 0.4 milliliters.

Vitamins, Minerals, Enzymes, and Amino Acids

The compositions of the present invention can include any of the water-soluble and/or fat-soluble vitamins, a coenzyme such as Q10, essential and/or non-essential amino acids (including standard and non-standard amino acids and their precursors), and minerals including without limitation calcium, phosphorus, magnesium, sodium, potassium, chloride, chromium, copper, fluoride, iodine, iron, manganese, molybdenum, selenium and zinc. The presently described technology can also include other ingredients, for example, nitrate, nitrite, folic acid, nucleic acids and their derivatives, amino acids and their derivatives, neurotransmitters and their precursors, plant extracts, additives, and adjuncts such as, but not limited to, caffeine. In addition, certain embodiments of the presently described ultra-low dose nutraceutical are substantially free of chloride compounds other than magnesium chloride.

The one or more components of the ultra-low dose nutraceutical compositions or formulations of the present invention can comprise at least five of the following ingredients or components: magnesium chloride, potassium carbonate, calcium ascorbate, ascorbic acid, caffeine, niacin, potassium benzoate, chromium picolinate, chromium, polynicotinate, coenzyme Q10, L-glutamine, potassium sorbate, calcium ascorbate, sodium nitrite, L-arginine, sodium ascorbate, copper, iron, potassium iodide, calcium carbonate, zinc, ascorbic acid, niacin, vitamin A, vitamin B1, vitamin B2, vitamin B3, vitamin B6, vitamin B12, vitamin C, vitamin D3, vitamin E, vitamin H, folic acid, Vitamin K, and combinations and derivatives thereof. Illustrative examples of ultra-low dose nutraceutical base mixtures and pre-mixes of the present invention are presented in U.S. Pat. No. 7,727,546, which is hereby incorporated by reference in its entirety.

Other forms of calcium may include, but are not limited to: Calcium ions, Calcium ascorbate, Calcium carbonate, Calcium chloride, Calcium phosphate. Other forms of magnesium include, but are not limited to: Magnesium ions, Magnesium oxide, Magnesium citrate, Magnesium chloride, Magnesium hydroxide, Magnesium sulfate, Magnesium aspartate, and Magnesium carbonate. Other forms of Potassium, include, but are not limited to: Potassium ions, Potassium carbonate, Potassium sorbate, Potassium chloride, Potassium benzoate, and Potassium iodide. Other forms of Sodium include, but are not limited to: Sodium ions, Sodium ascorbate, and Sodium nitrite. Other minerals include Selenium, Iodine, Copper, Molybdenum, and Phosphorus. Other antioxidants may include Glutathione and its derivatives and precursors. At least one embodiment of the present invention contains magnesium chloride, sodium ascorbate, potassium carbonate, calcium ascorbate, potassium sorbate, sodium nitrite, potassium benzoate, chromium picolinate, chromium polynicotinate, copper, iron, potassium iodide, calcium carbonate, zinc, ascorbic acid, niacin, vitamin A, vitamin B1, vitamin B2, vitamin B3, vitamin B6, vitamin B12, vitamin C, vitamin D3, vitamin E, vitamin H, folic acid, caffeine, L-glutamine, L-arginine, coenzyme Q10, and combinations and derivatives and precursors thereof.

In another embodiment, the nutraceutical/supplement composition/formulation of the present invention contains from about $1.25 \times 10^{-13}$ grams to about $3.5 \times 10^{-3}$ grams of at least one mineral, from about $6 \times 10^{-9}$ grams to about $6 \times 10^{-6}$ grams of at least one enzyme, from about $2 \times 10^{-14}$ grams to about $1.8 \times 10^{-4}$ grams of at least one vitamin, from about $3 \times 10^{-8}$ grams to about $3 \times 10^{-4}$ grams of at least one adjunct, and from about $1.5 \times 10^{-8}$ grams to about $1.5 \times 10^{-2}$ grams of at least one amino acid; and each compound/component can be, for example, in additional multiplied factors thereof, (e.g. ×0.0001, ×0.001, ×0.01, ×0.01, ×1, ×2, ×2.5, ×5, ×10, ×100, etc.).

Amino Acids

Amino acids and their precursors, analogues, and derivatives and alternative forms (L-, D- and DL-amino acids) may be added to the composition, including, but not limited the following: L-glutamine, L-arginine, tyrosine, tryptophan, glycine, L-theanine, lysine, L-aspartate, S-adenosyl-L-homocysteine (SAH), ornithine, theanine, and carnitine. Amino acids precursors are compounds that give amino acids after some reactions (usually hydrolysis). The amino acid glutamine is involved in many metabolic processes and it stabilizes the immune system, strengthens the intestinal cells and helps against stress, depression and anxiety. Glutamine increases the production of GABA, gamma-aminobutyric acid a neurotransmitter implicated in sleep. L-tryptophan stimulates the synthesis of serotonin, which is required for the neurotransmitter to induce sleep. Glycine functions as an inhibitory neurotransmitter in the central nervous system and acts as a co-agonist of glutamate receptors. L-theanine is an amino acid analogue demonstrates pharmacological actions such as promoting calmness and decreasing alertness. The amino acids glutamine, ornithine and arginine promote better sleep in that they decrease ammonia and stimulate liver detoxification. Carnitine serves as a mood enhancer, supports many brain functions and ensures better stress resistance.

Adjuncts and Additives

The compositions of the present invention may also include additives such as, but not limited to, the components described herein.

Film Forming Agents

Film forming agents include, but are not limited to, cellulose polymers, polyethylene oxide, pullulan, hydroxypropylmethyl cellulose, hydroxypropyl cellulose, polyvinyl pyrrolidone, polyvinyl alcohol, sodium alginate, polyethylene glycol, xanthan gum, tragacanth gum, guar gum, acacia gum, arabic gum, polyacrylic acid, amylase, starch, dextrin, pectin, chitin, chitosan, levan, elsinan, collagen, gelatin, zein, gluten, soy protein isolate, whey protein isolate, casein, and mixtures thereof.

The polymer may be water soluble, water swellable, water insoluble or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least about 20 percent by weight water uptake. Water swellable polymers having about 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly (lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/ glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of about 338° to about 347° F. (about 170° to about 175° C.); lactide/glycolide 100 L, believed to be 100% glycolide having a melting point within the range of about 437° to about 455° F. (about 225° to about 235° C.); lactide/glycolide 85/15, believed to be approximately 85% lactide and approximately 15% glycolide with a melting point within the range of about 338° to about 347° F. (about 170° to about 175° C.); and lactide/glycolide 50/50, believed to be a copolymer of about 50% lactide and about 50% glycolide with a melting point within the range of about 338° to about 347° F. (about 170° to about 175° C.). The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally, the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Flavors

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Useful flavors or flavoring agents include natural and artificial flavors. These flavorings may be chosen from synthetic flavor oils and flavoring aromatics, and/or oils, oleo resins and extracts derived from plants, leaves, flowers, fruits and so forth, and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. These flavorings can be used individually or in combination. Commonly used flavors include mints such as peppermint, artificial vanilla, cinnamon derivatives, and various fruit flavors, whether employed individually or in combination. Flavorings such as aldehydes and esters including cinnamylacetate, cinnamaldehyde, citral, diethylacetal, dihydrocarvyl acetate, eugenyl formate, p-methylanisole, and the like may also be used. Further examples of aldehyde flavorings include, but are not limited to acetaldehyde (apple); benzaldehyde (cherry, almond); cinnamicaldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 12,6-dimethyl-5-heptenal, i.e. melonal (melon); 2 dimethyloctanal (greenfruit); and 2-dodecenal (citrus, mandarin); cherry; grape; mixtures thereof; and the like.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The amount of flavoring employed is normally a matter of preference, subject to such factors as flavor type, individual flavor, and strength desired. The amount may be varied in order to obtain the result desired in the final product. Such variations are within the capabilities of those skilled in the art without the need for undue experimentation. In general, amounts of about 0.1 to about 30 weight (wt) % are useful with the practice of the present invention.

Sweeteners

Suitable sweeteners include both natural and artificial sweeteners. Non-limiting examples of suitable sweeteners include, e.g. water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin and the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenylglycine, L-aspartyl-2,5-dihydro-L-phenylalanine, L-aspartyl-L-(1-cyclohexyen)-alanine, and the like; water-soluble sweeteners derived from naturally occurring water-soluble sweeteners, such as a chlorinated derivatives of ordinary sugar (sucrose), known, for example, as sucralose; protein based sweeteners such as thaurnatoccous danielli (Thaurnatin I and II); and naturally occurring high intensity sweeteners, such as Lo Han Kuo, stevia, steviosides, monellin, and glycyrrhizin.

In general, an effective amount of auxiliary sweetener is utilized to provide the level of sweetness desired for a particular composition, and this amount will vary with the sweetener selected. This amount will normally be about 0.01% to about 10% by weight of the composition. These amounts may be used to achieve a desired level of sweetness independent from the flavor level achieved from any optional flavor oils used. Of course, sweeteners need not be added to films intended for non-oral administration.

Colorants

Color additives useful in this invention include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Other Additives or Fillers

A variety of other additives and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; thermo-setting gels such as pectin, carageenan, and gelatin, which help in maintaining the dispersion of components; and inclusion compounds, such as cyclodextrins and caged molecules, which improve the solubility and/or stability of certain active components.

The variety of additives that can be incorporated into the compositions of the present invention can provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer. Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

Additional compounds can be added to improve the flow properties of the starch material such as animal or vegetable fats, desirably in their hydrogenated form, especially those which are solid at room temperature. These fats desirably have a melting point of 50° C. or higher. Preferred are tri-glycerides with C12-, C14-, C16-, C18-, C20- and C22-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with C12-, C14-, C16-, C18-, C20- and C22-fatty acids.

The total amounts used of the fats, mono-, di-glycerides and/or lecithins are up to about 5% and preferably within the range of about 0.5% to about 2% by weight of the total composition.

It should be understood that in addition to the ingredients particularly mentioned above, the formulations of the present invention can include other suitable agents such as preservatives and antioxidants. Such antioxidants would be food acceptable and could include, for example, vitamin E, carotene, BHT or other antioxidants known to those of skill in the art.

Anti-Foaming and De-Foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

As a related matter, simethicone and related agents may be employed for densification purposes. More specifically, such agents may facilitate the removal of voids, air, moisture, and similar undesired components, thereby providing denser and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Plant Extracts

Plant extracts may be added, including, but not limited to Valerian (*Valeriana officinalis*), Passionflower (*Passiflora incarnata*), California Poppy (*Eschscholzia californica*), Ashwagandha (*Withania somnifera*), Magnolia Bark (*Magnolia officinalis*), Lavender (*Lavandula angustifolia, Lavandula officinalis*), Cannabis (*Cannabis sativa, Cannabis sativa* forma indica, *Cannabis ruderalis*), Hops (*Humulus lupulus*), and Chamomile (*Matricaria chamomilla* and *Chamaemelum nobile*).

Neurotransmitters

Neurotransmitters or neuropeptides may be added, including, but not limited to gamma-Aminobutyric acid (γ-Aminobutyric acid (GABA), 5-hydroxytryptamine (serotonin), hypocretin (orexin-A and -B), acetylcholine, norepinerphrine, Delta sleep-inducing peptide (DSIP), histamine and N-acetyl-5-methoxy tryptamine (Melatonin). A whole cocktail of neurotransmitters are involved in driving wakefulness and sleep, including histamine, dopamine, norepinephrine, serotonin, glutamate, orexin and acetylcholine, among others. While none of these neurotransmission processes is individually necessary, they all appear to contribute in some way. Histamine in particular is sometimes referred to as the "master" wakefulness-promoting neurotransmitter, exhibiting high activity during wakefulness, decreasing activity during non-REM sleep, and its lowest levels during REM sleep (which is why histamine-blocking antihistamine medications cause drowsiness and increase non-REM sleep). Serotonin activity promotes wakefulness, increases sleep-onset latency (the length of time it takes to fall asleep) and decreases REM sleep. Acetylcholine activity in the reticular activating system of the brainstem stimulates activity in the forebrain and cerebral cortex, encouraging alertness and wakefulness, although it also appears to be active during REM sleep. Another important chemical in the sleep-wake cycle is orexin (also called hypocretin), a neurotransmitter that regulates arousal, wakefulness and appetite. Orexin is only produced by some 10,000-20,000 neurons in the hypothalamus region of the brain, although axons from those neurons extend throughout the entire brain and spinal cord. Activation of orexin triggers wakefulness, while low levels of orexin at night serve to drive sleep.

Nucleotides

Nucleotides and their derivatives may be added, including, but not limited to adenosine 5'monophosphate (5'AMP), guanosine 5'monophosphate (5'GMP), and their precursor, inosine 5'monophosphate (5'IMP)—or a pyrimidine—uridine 5'monophosphate (5'UMP), cytidine 5'monophosphate (5'CMP), and thymidine 5'monophosphate (5'TMP), and adenosine. The nucleotides act in cells as secondary messengers through cAMP (cyclic 5'AMP) and cGMP (cyclic 5'GMP), and also supply the necessary chemical energy. They can also act as components of many enzyme co-factors such as flavin adenine dinucleotide (FAD) and nicotinamide adenine dinucleotide (NAD), in addition to having a strong influence on sleep. 5'UMP, is distributed throughout the body (including the brain), and has a depressive effect on the CNS. The nightly administration of low doses of this nucleotide produces a moderate increase in the number of REM and non-REM sleep episodes, 4 but has little or no influence on their duration. The plasma concentration of uridine in mice has a marked circadian rhythm, with the time of the maximum concentration (acrophase) coinciding with the time of least activity. 5'AMP, is the nucleotide which is most referred to in the literature as a sleep inducer. More recent evidence confirming its role in sleep induction is based on several facts: extracellular concentrations (through the secondary messenger cAMP) present circadian variations, its administration induces an hypnotic effect, and its levels decline during the period of wakefulness. 5'GMP, is also a second messenger in its cyclic form (cGMP), which mediates most of the neuronal effects of nitric oxide (NO). Many studies have pointed to the role of NO in sedation. For instance, the injection of a cGMP inhibitor into rats was found to increase wakefulness at the same time as suppressing REM and non-REM sleep. 12 Human studies have shown that cGMP plasma concentrations rise when the subject goes to bed and remain high throughout the night, reflecting its role in stimulating the secretion of the pineal hormone melatonin.

Delivery System(s)

For the present invention, any dosage form can be utilized. Those dosage forms can include, for example, an oral film, tablet, pill, liquid, sublingual liquid, capsule, lozenge, troche, suppository, transdermal patch, oral spray, nasal sprays, dragée, slurry, suspension, or emulsion. For this particular technology, dosage administration routes are preferably those that by-pass first pass metabolism such as sublingual, buccal, nasal, transdermal, intradermal, intramuscular, intravenous, and certain rectal routes. Again, without being bound by any particular theory this is due to the present invention being believed to have enhanced efficacy by circumventing dosage administration routes which would undergo first pass metabolism (gastrointestinal, in particular).

Compositions of the present invention can be preferably formulated for parenteral absorption. Parenteral absorption generally comprises absorption by way other than the gastrointestinal track and without significant first pass metabolism. By way of example and without limitation, parenteral absorption can be pre-gastric, topical, optical, intravenous, and/or by oral or nasal inhalation. Pre-gastric absorption as used herein comprises absorption of an ingredient, composition, or formulation of the present invention from that part of the alimentary canal prior to the stomach, and includes without limitation buccal, sublingual, oropharyngeal and esophageal absorption. It is envisaged that such pre-gastric absorption will occur primarily across the mucous membranes in the mouth, pharynx and esophagus. The oral mucosa has a thin epithelium and a rich vascularity that favors absorption. Blood capillaries are extremely close to the surface in these areas and readily absorb the ingredients into the blood stream. The flow is from this area of the mouth to the Carotid Artery and it is envisaged that distribution to the brain and the rest of the body will be rapid, thereby resulting in greatly enhanced efficacy and/or rates of response. The present invention, however, is not limited to any one method of delivery, and envisions delivery via any tissue with an adequate rate of absorption, which avoids first pass metabolism.

It is further believed that ingredients absorbed by pre-gastric absorption will pass substantially into the systemic circulatory system and thereby avoid the gastrointestinal track and first pass metabolism in the liver. Accordingly, bioavailability of one or more active ingredients, additives, adjuncts and the like of the present invention delivered in this way may also be increased. Additionally, the bioavailability of a number of vitamins, minerals, amino acids, co-enzymes, and/or other nutrients in concert can also be increased. It is desired and in some embodiments preferred that the dose of an ingredient/component may be minimized, while still producing the desired beneficial effects, with close to zero order kinetics (immediate efficacy) thereby decreasing the required dose. These concentrations may vary and will be selected primarily on the desired biological response and dosage form selected, especially those related directly or indirectly to or for sleep and/or sleep disorders.

U.S. Pat. Nos. 6,596,298; 6,569,463; 5,948,430; 6,592,887; 5,629,003; 6,419,903; and 6,316,029 disclose various delivery systems which may be utilized in the practice of the present invention.

One particularly preferred method of delivery, although the present invention is not limited to any one method, is a sublingual liquid provided in a volume of from about 0.15 milliliters to about 0.4 milliliters. Additional information regarding the dosage forms and levels of the presently described technology are presented in U.S. Pat. No. 7,727,546, which is hereby incorporated by reference in its entirety.

Biological Responses/Sleep/Sleep Disorders

In one or more embodiments of the present invention, the particular biological response is enhanced sleep quality. "Enhanced sleep quality" is defined herein as a period of sleep characterized by decreased ratio of stage 1 sleep to DELTA sleep, decreased ratio of stage 1 sleep to REM sleep, decreased number of awakenings, decreased number of arousals, decreased latencies, decreased number of sleep disorder events such as, but not limited to, apneic events, and/or any other outcomes that would be recognized as enhancing sleep quality by one of ordinary skill in the field of sleep studies. In another embodiment of the present invention, the nutraceutical composition/formulation is used to treat a sleep disorder including, but not limited to, sleep apnea.

Specifically, sublingual administration of the nutraceutical composition/formulation presented in Table 1 produced potentially clinically significant results on a range of sleep dysfunctions including: a shift in percentage time spent in REM and DELTA sleep vs. Stage 1 sleep, a reduction in sleep apnea events for those with clinical sleep apnea, reductions in awakenings and arousals, and reductions in sleep latencies.

TABLE 1

| Sleep Enhancing Nutraceutical Composition/Formulation 1 | | | |
|---|---|---|---|
| Ingredient | Grams Per 0.20 milliliter Dose (A20) | Grams Per 0.25 milliliter Dose (A25) | Grams Per 0.30 milliliter Dose (A30) |
| Magnesium Chloride | 0.000000436 | ≈0.0000005445343474 | 0.000000654 |
| Sodium Ascorbate | 6.536E−07 | ≈0.0000008168015210 | 9.804E−07 |
| Potassium Carbonate | 6.536E−07 | ≈0.0000008168015210 | 9.804E−07 |
| Calcium Ascorbate | 0.000000436 | ≈0.0000005445343474 | 0.000000654 |
| Ascorbic Acid (ester C) | 0.000003632 | ≈0.0000045377862280 | 0.000005448 |
| Caffeine | 6.896E−07 | ≈0.0000008621793833 | 1.0344E−06 |
| Niacin | 7.264E−08 | ≈0.0000000907557246 | 1.0896E−07 |
| Potassium Benzoate | 3.264E−07 | ≈0.0000004084007605 | 4.896E−07 |
| Chromium Picolinate | 1.36E−09 | ≈0.0000000016971320 | 2.04E−09 |
| Chromium polynicotinate | 1.36E−09 | ≈0.0000000016971320 | 2.04E−09 |
| Coenzyme Q10 | 4.536E−07 | ≈0.0000005672232785 | 6.804E−07 |
| L-Glutamine | 0.000001816 | ≈0.0000022688931140 | 0.000002724 |
| L-Arginine | 0.000001816 | ≈0.0000022688931140 | 0.000002724 |
| Potassium Sorbate | 7.264E−07 | ≈0.0000009075572456 | 1.0896E−06 |
| Sodium Nitrite | 5.264E−07 | ≈0.0000006579790031 | 7.896E−07 |
| Vitamin A | 7.488E−08 | ≈0.0000000935591919 | 1.1232E−07 |
| Vitamin B1 | 1.312E−09 | ≈0.0000000016354938 | 1.968E−09 |
| Vitamin B2 | 9.92E−10 | ≈0.0000000012352863 | 1.488E−09 |
| Vitamin B3 | 1.264E−08 | ≈0.0000000157562022 | 1.896E−08 |
| Vitamin B6 | 1.264E−08 | ≈0.0000000157562024 | 1.896E−08 |
| Vitamin B12 | 3.784E−12 | ≈0.0000000000047269 | 5.676E−12 |
| Vitamin C | 3.784E−08 | ≈0.0000000472686065 | 5.676E−08 |
| Vitamin D3 | 5.984E−09 | ≈0.0000000074847354 | 8.976E−09 |
| Vitamin E | 4.368E−10 | ≈0.0000000005457620 | 6.552E−10 |
| Vitamin H | 1.136E−10 | ≈0.0000000001418058 | 1.704E−10 |
| Folic Acid | 1.208E−10 | ≈0.0000000001512595 | 1.812E−10 |
| Copper | 5.544E−10 | ≈0.0000000006932729 | 8.316E−10 |
| Iron | 4.816E−09 | ≈0.0000000060188692 | 7.224E−09 |
| Potassium Iodide | 4.144E+11 | ≈0.0000000000517612 | 6.216E+11 |
| Calcium Carbonate | 2.52E−08 | ≈0.0000000315124044 | 3.78E−08 |
| Zinc | 4.056E−09 | ≈0.0000000050734971 | 6.084E−09 |

In another embodiment of the present invention, enhanced sleep quality may be induced by administration of the nutraceutical formulation/composition presented in Table 2.

TABLE 2

Sleep Enhancing Nutraceutical Composition/Formulation 2

| Ingredient | Grams Per 0.20 milliliter Dose (A20) | Grams Per 0.25 milliliter Dose | Grams Per 0.30 milliliter Dose (A30) |
|---|---|---|---|
| Magnesium Chloride | 7.29E−08 | ≈0.000000091139356347618000 | 1.09E−07 |
| Sodium Ascorbate | 1.10E−07 | ≈0.000000136709034521427000 | 1.64E−07 |
| Potassium Carbonate | 1.10E−07 | ≈0.000000136709034521427000 | 1.64E−07 |
| Calcium Ascorbate | 7.29E−08 | ≈0.000000091139356347618000 | 1.09E−07 |
| Ascorbic Acid (ester C) | 6.07E−07 | ≈0.000000759494636230150000 | 9.11E−07 |
| Caffeine | 1.15E−07 | ≈0.000000144303980883729000 | 1.73E−07 |
| Niacin | 1.22E−08 | ≈0.000000015189892724603000 | 1.82E−08 |
| Potassium Benzoate | 5.47E−08 | ≈0.000000068354517260713500 | 8.21E−08 |
| Chromium Picolinate | 2.27E−10 | ≈0.000000000284050993950080 | 3.41E−10 |
| Chromium polynicotinate | 2.27E−10 | ≈0.000000000284050993950080 | 3.41E−10 |
| Coenzyme Q10 | 7.59E−08 | ≈0.000000094936829528768700 | 1.14E−07 |
| L-Glutamine | 3.04E−07 | ≈0.000000379747318115075000 | 4.56E−07 |
| L-Arginine | 3.04E−07 | ≈0.000000379747318115075000 | 4.56E−07 |
| Potassium Sorbate | 1.22E−07 | ≈0.000000151898927246030000 | 1.82E−07 |
| Sodium Nitrite | 8.80E−08 | ≈0.000000110126722253372000 | 1.32E−07 |
| Vitamin A | 1.26E−08 | ≈0.000000015659112358202900 | 1.88E−08 |
| Vitamin B1 | 2.19E−10 | ≈0.000000000273734525141280 | 3.29E−10 |
| Vitamin B2 | 1.66E−10 | ≈0.000000000206751317640430 | 2.48E−10 |
| Vitamin B3 | 2.11E−09 | ≈0.000000002637134153576910 | 3.17E−09 |
| Vitamin B6 | 2.11E−09 | ≈0.000000002637134182929360 | 3.17E−09 |
| Vitamin B12 | 6.33E−13 | ≈0.000000000000791140246070 | 9.49E−13 |
| Vitamin C | 6.33E−09 | ≈0.000000007911402460730750 | 9.49E−09 |
| Vitamin D3 | 1.00E−09 | ≈0.000000001252728988630730 | 1.50E−09 |
| Vitamin E | 7.30E−11 | ≈0.000000000091344822087660 | 1.10E−10 |
| Vitamin H | 1.90E−11 | ≈0.000000000023734207382190 | 2.84E−11 |
| Folic Acid | 2.02E−11 | ≈0.000000000025316487872140 | 3.04E−11 |
| Copper | 9.28E−11 | ≈0.000000000116033902757090 | 1.39E−10 |
| Iron | 8.08E−10 | ≈0.000000001007385246666230 | 1.21E−09 |
| Potassium Iodide | 6.93E−12 | ≈0.000000000008663329668300 | 1.04E−11 |
| Calcium Carbonate | 2.40E+11 | ≈0.000000005274268307153090 | 3.60E+11 |
| Zinc | 6.79E−10 | ≈0.000000000849157197393060 | 1.02E−09 |

Each constituent in the formulation A20 and Table 2 may be increased or decreased by at least 5%, 15%, 25%, 50%, 75%, 100%, 125%, 150%, 175%, or 200% to enhance sleep quality.

In an additional embodiment of the present invention, the particular biological response is a short duration sleep, or nap, that is induced by administration of the nutraceutical formulation/composition presented in Table 3.

TABLE 3

Nap/Short Duration Sleep Enhancing Nutraceutical Formulation1

| Ingredient | Grams Per 0.25 milliliter Dose |
|---|---|
| Magnesium Chloride | ≈0.0000003614166022 |
| Sodium Ascorbate | ≈0.0000005421249033 |
| Potassium Carbonate | ≈0.0000005421249033 |
| Calcium Ascorbate | ≈0.0000003614166022 |
| Ascorbic Acid (ester C) | ≈0.0000030118050186 |
| Caffeine | ≈0.0000005722429535 |
| Niacin | ≈0.0000000602361004 |
| Potassium Benzoate | ≈0.0000002710624517 |
| Chromium Picolinate | ≈0.0000000011264151 |
| Chromium polynicotinate | ≈0.0000000011264151 |
| Coenzyme Q10 | ≈0.0000003764756273 |
| L-Glutamine | ≈0.0000015059025093 |
| L-Arginine | ≈0.0000015059025093 |
| Potassium Sorbate | ≈0.0000006023610037 |
| Sodium Nitrite | ≈0.0000004367117277 |
| Vitamin A | ≈0.0000000620968088 |
| Vitamin B1 | ≈0.0000000010855047 |
| Vitamin B2 | ≈0.0000000008198803 |
| Vitamin B3 | ≈0.0000000104576563 |
| Vitamin B6 | ≈0.0000000104576564 |
| Vitamin B12 | ≈0.0000000000031373 |
| Vitamin C | ≈0.0000000313729689 |
| Vitamin D3 | ≈0.0000000049677447 |
| Vitamin E | ≈0.0000000003622314 |
| Vitamin H | ≈0.0000000000941189 |
| Folic Acid | ≈0.0000000001003935 |
| Copper | ≈0.0000000004601369 |
| Iron | ≈0.0000000039948247 |
| Potassium Iodide | ≈0.0000000000343548 |
| Calcium Carbonate | ≈0.0000000209153126 |
| Zinc | ≈0.0000000033673653 |

In a further embodiment of the present invention, the short duration sleep, or nap, may be induced by administration of the nutraceutical formulation/composition presented in Table 4.

TABLE 4

Nap/Short Duration Sleep Enhancing Nutraceutical Formulation 2

| Ingredient | Grams Per 0.25 milliliter Dose |
|---|---|
| Magnesium Chloride | ≈0.00000000607899506838612 0 |
| Sodium Ascorbate | ≈0.0000000911849260257918 0 |
| Potassium Carbonate | ≈0.0000000911849260257918 0 |
| Calcium Ascorbate | ≈0.00000000607899506838612 0 |
| Ascorbic Acid (ester C) | ≈0.000000050658292236551000 |
| Caffeine | ≈0.000000096250755249446 90 |
| Niacin | ≈0.000000010131658447310 20 |
| Potassium Benzoate | ≈0.000000045592463012895 90 |
| Chromium Picolinate | ≈0.000000000189462012964 70 |
| Chromium polynicotinate | ≈0.000000000189462012964 70 |
| Coenzyme Q10 | ≈0.000000063322865295688 80 |

TABLE 4-continued

Nap/Short Duration Sleep Enhancing Nutraceutical Formulation 2

| Ingredient | Grams Per 0.25 milliliter Dose |
| --- | --- |
| L-Glutamine | ≈0.000000253291461182755000 |
| L-Arginine | ≈0.000000253291461182755000 |
| Potassium Sorbate | ≈0.000000101316584473102000 |
| Sodium Nitrite | ≈0.000000073454523742999000 |
| Vitamin A | ≈0.000000010444627942921300 |
| Vitamin B1 | ≈0.000000000182580928269240 |
| Vitamin B2 | ≈0.000000000137903128866170 |
| Vitamin B3 | ≈0.000000001758968480435800 |
| Vitamin B6 | ≈0.000000001758968500013880 |
| Vitamin B12 | ≈0.000000000000527690544130 |
| Vitamin C | ≈0.000000005276905441307410 |
| Vitamin D3 | ≈0.000000000835570235416700 |
| Vitamin E | ≈0.000000000060926996332470 |
| Vitamin H | ≈0.000000000015830716323920 |
| Folic Acid | ≈0.000000000016886097410720 |
| Copper | ≈0.000000000077394613138980 |
| Iron | ≈0.000000000671925959526380 |
| Potassium Iodide | ≈0.000000000005778440888760 |
| Calcium Carbonate | ≈0.000000003517936960871110 |
| Zinc | ≈0.000000000566387850661170 |

Each constituent in the formulation in Tables 3 and 4 may be increased or decreased by at least 5%, 15%, 25%, 50%, 75%, 100%, 125%, 150%, 175%, or 200% to enhance short duration sleep or naps.

Without wishing to be bound by any particular theory, it is believed, given the components, ingredients, additives, adjuncts and the like present in the nutraceutical formulations/compositions and the extremely small dosages of such components/ingredients, etc., that the mechanism by which the nutraceutical compositions/formulations of the present invention elicit effects on sleep is not a systemic mechanism, but rather a central mechanism.

The following examples describe some of the preferred embodiments of the present invention without limiting the technology thereto. Other embodiments include, but are not limited to, those described in the above written description, including additional or alternative components, alternative concentrations, and additional or alternative properties and uses.

EXAMPLE

With respect to a design of experiment of a larger scale study, the data suggests that time in REM sleep, total sleep time, sleep efficiency (as a percentage of total time in bed) and REM latency (the average time between start of sleeping and start of REM sleep) are likely candidate factors for evaluating the effect of administration of the composition of the invention on sleep. In addition to these factors, as the stage n3-NREM sleep is known to be implicated in glymphatic system activation, that factor should be studied as well.

Nutraceutical Composition/Formulation for Enhanced Sleep Quality and Treatment of Sleep Disorders Pilot Studies: Sleep Studies Design For each pilot study 12 healthy adults, (Pilot 1—1 man & 11 women; Pilot 2 8 men and 4 women) were recruited. These studies followed a double-blind placebo control design, each participant acted as their own control. An independent tester only was aware of the contents of the 3-bracketed doses (200 µL, 250 µL, or 300 µL) of the formulation presented in Table 1. (1 of 2 dosages or the placebo). The independent tester broke the code after the data was collected and analyzed. The subjects were monitored on the first night in order to establish a baseline polysomnography (PSG). The only difference between the participants recruited for these 2 studies was that individuals recruited for Pilot 2 had to report symptoms consistent with moderate to severe sleep disturbances whereas those in Pilot 1 anyone with reported "poor" sleep was included. All of the individuals recruited did not have a known diagnosed sleep disorder, but reported one or more of the following symptoms: frequent waking, difficulty falling asleep, restlessness, and/or upon waking feeling fatigued. Individuals were at least 18 years of age, generally in good health (no known cardiovascular, pulmonary, neurological, or metabolic disease), no recent or current use of any sleep aid (prescription, over-the-counter, herbal) nonsmoker, available for four consecutive nights, no significant project/assignment/exam due or atypical stressor, body mass index (BMI)<30, and have not previously participated in a formal sleep study. The study took place in quiet rooms. Separated rooms were utilized so that the sleep technician could set up equipment in the common room and conduct the sleep study on two participants at once. In the clinically setting this 1:2 ratio is considered standard practice. Each participant had his or her own bedroom and bathroom.

For both Pilot 1 and 2, on each of the four nights, the participant was asked to arrive approximately 1 hour before he or she would normally go to bed and maintain their normal schedule and routine as much as possible. Upon arrival, each participant was given a short survey to determine how he or she felt during their previous night's sleep and how the previous night's sleep affected their day's activities. Preparation for the sleep study included: placing EEG (electroencephalogram) on the participant's scalp, EMG (electromyogram) electrodes on the outer edge of their eyelids, chin and lower legs, and ECG (electrocardiogram) in a 3 lead pattern on the participant's chest. These electrodes remained in place while the participant slept and were used to monitor brain activity, facial muscle activity and heart activity. Respiration was measured with a light plastic wire and a thermometer positioned at the base of the nose. Elastic webbing around the chest and abdomen were used to record breathing and body movement. Pulse oximetry (finger) was used to monitor blood oxygen content. The licensed polysomnographic technologist prepared the participant and was on duty throughout the overnight stay. Once the participant was properly prepared, they were instructed to go to bed and follow their normal pattern of behavior (watching TV, reading, etc.) including lights out at their normal bedtime.

On the first night, the participants received neither the nutraceutical composition/formulation (Table 1) or the placebo. On the subsequent three nights each subject received, in a predetermined randomized order. In Pilot 1 each participant received randomly a 200 µL (A20) and 250 µL (A25) dose of the nutraceutical composition/formulation as presented in Table 1, whereas in Pilot 2, A25 and 300 µL (A30) dosages were used. In both Pilots a 0.250 µL of the placebo (sterilized distilled water) was utilized. Multiple dosages were tested in order to bracket and identify the potential effective dosage range(s). Thus, upon completion of the four-night PSG study, a baseline (B), placebo (P), and 2 nutraceutical composition/formulation (Table 1) (A20/A25 or A25/A30) had been recorded for each participant. The investigator administered the liquid nutraceutical composition/formulation (Table 1) and placebo sublingually, via a pipet, and the subject was instructed not to swallow for 60 seconds. The participants were told only that 3 different formulations were being used and were only told about the use of the placebo at the completion of the study. Upon waking in the morning, the sleep technician removed all of the electrodes and completed a short survey documenting the subject's sleep.

Analysis of Pilot 1 results revealed that the nutraceutical composition/formulation (Table 1) was most effective when administered to participants with the poorest baseline sleep quality (A20 and A25). Therefore, Pilot 2 was performed on individuals who suffered from self-reported moderate to severe sleep dysfunction.

Statistics

Statistical analysis was performed independently for Pilot 1 (dose bracket A20 and A25) and Pilot 2 (dose bracket A25 and A30). A statistical analysis was also performed for dose bracket A25 with the 6 subjects from the Pilot 1 who exhibited the highest level of sleep dysfunction together with all 12 of the subjects from the Pilot 2 (n=18). As a preliminary finding, dose bracket A20 appears to have to greatest effect with regard to overall sleep quality, the time in REM sleep, total sleep time, sleep efficiency (as a percentage of total time in bed) and REM latency (the average time between start of sleeping and start of REM sleep) were found to have the greatest significance on overall sleep quality. Whereas dose bracket A30 demonstrated the least effectiveness and will not be reported. However, it is noted that dose bracket A30 appeared to affect the clinical appearance of sleep apnea in those (n=3) with documented severe obstructive apnea.

Total Sleep

Analysis of the results from the data of Pilots revealed that when participants received the A20 nutraceutical composition/formulation presented in Table 1, a significant increase in total sleep was observed (Table 5). This was not the case for A25 nor A30 (Pilot 2) therefore Pilot 2 data has not been reported.

TABLE 5

Total Sleep (minutes)

| | n | Mean | STDev | df | p |
|---|---|---|---|---|---|
| Pilot 1 Baseline | 12 | 385.99 | 29.08 | | |
| Placebo | 12 | 383.95 | 29.32 | 11 | 0.767 |
| A20 | 12 | 420.54 | 45.68 | 11 | 0.009* |
| A25 | 12 | 386.71 | 41.34 | 11 | 0.945 |

*Statistically significant.

Arousals and Arousals/Awakenings

Analysis of the results from the two pilots revealed that when the nutraceutical composition/formulation presented in Table 1 was administered, a clear trend towards a lower number of arousals and fewer total arousals/awakenings was observed with A20 (Tables 6 & 9). The data for A25 was combined from Pilots 1 and 2, however the results were not significant (Tables 7 & 8) Overall a large amount of inter-subject variability was also observed for these variables. This was not the case for A30 (Pilot 2) therefore the data has not been reported.

TABLE 6

Number of Arousals

| | n | Mean | STDev | df | p |
|---|---|---|---|---|---|
| Pilot 1 Baseline | 12 | 183.83 | 44.09 | | |
| Placebo | 12 | 176.83 | 64.62 | 11 | 0.626 |
| A20 | 12 | 165.83 | 31.59 | 11 | 0.118 |
| A25 | 12 | 156.50 | 48.49 | 11 | 0.074 |

TABLE 7

Number of Arousals (Combined Pilot 1 and 2)

| | n | Mean | STDev | df | p |
|---|---|---|---|---|---|
| Placebo | 18 | 270.44 | 145.24 | | |
| A25 | 18 | 248.44 | 144.24 | 17 | 0.177 |

TABLE 8

Arousal Index (Combined Pilot 1 and 2)

| | n | Mean | STDev | df | p |
|---|---|---|---|---|---|
| Placebo | 18 | 40.27 | 19.85 | | |
| A25 | 18 | 36.78 | 17.31 | 17 | 0.129 |

TABLE 9

Number of Arousals/Awakenings

| | n | Mean | STDev | df | p |
|---|---|---|---|---|---|
| Pilot 1 Baseline | 12 | 189.58 | 43.77 | | |
| Placebo | 12 | 180.08 | 64.28 | 11 | 0.523 |
| A20 | 12 | 1659.17 | 33.01 | 11 | 0.081 |
| A25 | 12 | 160.50 | 50.86 | 11 | 0.066 |

Latency

Analysis of the second sleep study results revealed some significant inter-subject variability, and a significant trend towards the subjects attaining the first bout of REM sleep in a lesser amount of time (decreased REM latency) when the composition/formulation presented in Table 1 was administered (Tables 10). The data for A25 was combined from Pilots 1 and 2, however the results were not significant (Table 11) possibly due to the large amount of inter-subject variability for this variable. This was not the case for A30 (Pilot 2) therefore the data has not been reported.

TABLE 10

Latency to First Bout REM (minutes)

| | n | Mean | STDev | df | p |
|---|---|---|---|---|---|
| Pilot 1 Baseline | 12 | 133.54 | 72.01 | | |
| Placebo | 12 | 98.63 | 68.59 | 11 | 0.654 |
| A20 | 12 | 97.58 | 50.49 | 11 | 0.019* |
| A25 | 12 | 85.41 | 37.64 | 11 | 0.014* |

*Statistically significant.

TABLE 11

Latency to First Bout REM (minutes) (Combined Pilot 1 and 2)

|  | n | Mean | STDEV | df | p |
|---|---|---|---|---|---|
| Placebo | 18 | 96.86 | 61.07 | | |
| A25 | 18 | 82.06 | 33.17 | 17 | 0.099 |

DELTA and REM Sleep Time

Further analysis of the sleep study data revealed a trend (significant for REM and the A20 dose) towards an increase in the absolute number of minutes in DELTA and REM when subjects were administered the nutraceutical presented in Table 1. This is important because the longer DELTA and REM sleep stages indicate better sleep quality and more restorative sleep (Tables 11 & 12). This was not the case for A30 (Pilot 2) therefore the data has not been reported.

TABLE 12

Sleep Time DELTA

|  | n | Mean | STDev | df | p |
|---|---|---|---|---|---|
| Pilot 1 Baseline | 12 | 77.67 | 32.22 | | |
| Placebo | 12 | 77.71 | 35.45 | 11 | 0.996 |
| A20 | 12 | 87.04 | 28.85 | 11 | 0.184 |
| A25 | 12 | 88.00 | 36.13 | 11 | 0.368 |

*Statistically significant.

TABLE 13

Sleep Time REM

|  | n | Mean | STDev | df | p |
|---|---|---|---|---|---|
| Pilot 1 Baseline | 12 | 58.13 | 18.94 | | |
| Placebo | 12 | 66.75 | 19.75 | 11 | 0.120 |
| A20 | 12 | 77.92 | 18.86 | 11 | 0.006* |
| A25 | 12 | 68.42 | 14.51 | 11 | 0.217 |

Dysfunction Indices

The Apnea Index shows that all but one of the participants in the Pilot 2 demonstrated some level of sleep apnea, while three subjects demonstrated clinical sleep apnea. The data from the three subjects with clinical sleep apnea demonstrated drops in apneic events. Analysis of the data also revealed, despite the inter-subject variability, that those subjects with the greatest sleep apnea issues appeared to have a positive effect from the administration of the tested nutraceutical composition/formulation presented in. While statistical analysis is not appropriate for a n=3, it is demonstrated that for the majority of the variables assessed for the three individuals with clinically documented apnea showed clinically important improvements with the introduction of the nutraceutical presented in Table 1 versus the placebo. In particular, note the decreased number of apneas and change in the apnea index. Two of the three subjects experienced a decrease in the number of arousals, and a decrease in the arousal index. It is also important to note the varying dosage related effects. While no variable from this analysis demonstrates a significant difference, the mean differences between the variables illustrate that administration of the nutraceutical composition/formulation presented in Table 1 elicits a trend towards clinical effectiveness for enhancing sleep quality and the potential that different dosages may be required for specific sleep disturbance types.

Relative Significance of Sleep Stages & Design of Experiments (DOE)

The two pilot studies were undertaken to test the relative significance of sleep stages 2, 3-NREM, REM, total sleep, number of arousals, sleep efficiency and REM latency. The purpose of the pilot studies was three-fold: first, to assess the relative significance of each factor on sleep quality and second, as a basis for a design of experiment for a larger scale study to test those factors that are likely implicated in assessing central nervous system effect of administration of the composition of the present invention and third look at a dose response relationship. As is reflected in the Table 14, pilot study 1 evaluated twelve patients for each of the enumerated factors. The data from Pilot 1, A20, was selected to construct the sample size calculations due to the fact that the participants self-report mild to severe sleep dysfunction whereas in Pilot 2 we excluded those with mild symptoms. The justification is that Pilot 1 better represents the population of those with sleep dysfunction and demonstrated the greatest within participate variability.

With the interest in enhancing NREM sleep Table 14 demonstrates that a sample size of approximately 65, would be sufficient to test the hypotheses that the A20 (the lowest concentration evaluated) formulation of nutraceutical composition/formulation (Table 1), significantly increases the total number of minutes of NREM sleep and the percentage of NREM as a fraction of total sleep. The sample size calculation also predicts that approximately 46 individuals would be required to demonstrate a significant reduction in arousals. Having each participant acting as their own control was necessary due to the small sample size in these pilot studies, however in a larger, formal clinical trial subjects would be randomized into experimental groups receiving only the placebo or the product. This methodology would significantly reduce the variability found between and across subjects in the Pilot work.

TABLE 14

| Variable | n | Variable mean | Variable STDev | Baseline Mean | Baseline STDev | $R^2$ | Pilot Sig. | Effect Size | Estimated Sample Size | Expected Actual Power |
|---|---|---|---|---|---|---|---|---|---|---|
| Stage II A20 (min) | 12 | 211.333 | 37.955 | 204.000 | 25.109 | 0.542 | 0.447 | 0.228 | 205 | 0.900 |
| Stage III-NREM A20 (min) | 12 | 87.042 | 28.853 | 77.667 | 32.220 | 0.723 | 0.184 | 0.409 | 65 | 0.900 |
| REM A20 (min) | 12 | 77.917 | 18.855 | 58.125 | 18.944 | 0.419 | 0.006* | 0.971 | 14 | 0.919 |
| Total Sleep A20 (min) | 12 | 420.542 | 45.686 | 385.958 | 29.082 | 0.575 | 0.009* | 0.923 | 15 | 0.913 |

TABLE 14-continued

| Variable | n | Variable mean | Variable STDev | Baseline Mean | Baseline STDev | $R^2$ | Pilot Sig. | Effect Size | Estimated Sample Size | Expected Actual Power |
|---|---|---|---|---|---|---|---|---|---|---|
| Arousals A20 (total) | 12 | 165.833 | 31.588 | 183.833 | 44.095 | 0.570 | 0.118 | 0.489 | 46 | 0.900 |
| Sleep Efficiency A20 (%) | 12 | 93.675 | 4.2425 | 89.058 | 5.850 | 0.716 | 0.002* | 0.944 | 14 | 0.903 |
| REM Latency A20 (min) | 12 | 97.583 | 50.487 | 133.542 | 72.039 | 0.784 | 0.019* | 0.797 | 19 | 0.902 |

A20 = 200 µL dose of the inventive formulation presented in Table 1, n = pilot study sample size; $R^2$ = Correlation between groups (Baseline & Variable); Effect Size = Using Baseline & Variable; Expected Sample Size = –Minimum sample size required for Clinical Trial; Expected Actual Power (with p = 0.05) = Expected power for Study;
*= Significant in Pilot A20 (p ≤ 0.05).

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

The invention claimed is:

1. A nutraceutical composition comprising micro- or nano-quantities of the following ingredients in a preparation suitable for administration to a person in need thereof, the ingredients comprising, in combination with minerals or salts thereof comprising magnesium, sodium, potassium, calcium, chromium, copper, iron and zinc, vitamins comprising A, B1, B2, B3, B6, B12, folic acid, C, D3, E and H, at least one antioxidant, and at least one amino acid, wherein the minerals comprise, in combination, magnesium chloride, sodium ascorbate, sodium nitrite, potassium carbonate, calcium ascorbate, potassium benzoate, chromium picolinate, chromium polynicotinate, potassium sorbate, potassium iodide, calcium carbonate, iron, copper and zinc.

2. The nutraceutical composition of claim 1, wherein the at least one antioxidant is coenzyme Q-10.

3. The nutraceutical composition of claim 1, wherein the at least one amino acid is L-glutamine or L-arginine.

4. A nutraceutical composition comprising, in combination, magnesium or salts thereof, sodium or salts thereof, potassium or salts thereof, calcium or salts thereof, chromium, copper, iron and zinc, vitamins A, B1, B2, B3, B6, B12, folic acid, C, D3, E and H, at least one antioxidant, L-glutamine and L-arginine, wherein each of the foregoing is present in micro- or nano-quantities in a preparation suitable for oral administration to a person in need thereof, wherein the minerals comprise, in combination, magnesium chloride, sodium ascorbate, sodium nitrite, potassium carbonate, calcium ascorbate, potassium benzoate, chromium picolinate, chromium polynicotinate, potassium sorbate, potassium iodide, calcium carbonate, iron, copper and zinc.

5. The nutraceutical composition of claim 4, wherein the nutraceutical is administered to an individual to induce enhanced sleep quality in the individual.

6. The nutraceutical composition of claim 4, wherein the nutraceutical composition substantially avoids first pass metabolism when administered to a person in need thereof.

7. The nutraceutical composition of claim 4, wherein the nutraceutical composition is administered to an individual to induce stage n3-NREM sleep.

8. The composition of claim 4, wherein the short duration sleep lasts for about one hour or less.

9. A method of activating a subject's glymphatic system, comprising the step of administering a therapeutically effective amount of the composition of claim 1 by a route of administration that substantially avoids first pass metabolism.

10. A method of activating a subject's glymphatic system, comprising the step of administering a therapeutically effective amount of the composition of claim 4 by a route of administration that substantially avoids first pass metabolism.

11. A nutraceutical composition comprising micro- or nano-quantities of the following ingredients in an oral preparation suitable for oral administration to a person in need thereof, the ingredients comprising, in combination with minerals or salts thereof comprising magnesium, sodium, potassium, calcium, chromium, copper, iron and zinc, vitamins comprising A, B1, B2, B3, B6, B12, folic acid, C, D3, E and H, at least one antioxidant, and at least one amino acid, wherein the at least one amino acid is L-arginine.

12. The nutraceutical composition of claim 11, wherein the minerals further comprise a chloride, a carbonate, an ascorbate, a nitrite, a picolinate, a polynicotinate, a benzoate or an iodide.

13. The nutraceutical composition of claim 11, wherein the minerals comprise, in combination, magnesium chloride, sodium ascorbate, sodium nitrite, potassium carbonate, calcium ascorbate, potassium benzoate, chromium picolinate, chromium polynicotinate, potassium sorbate, potassium iodide, calcium carbonate, iron, copper and zinc.

14. The nutraceutical composition of claim 11, wherein the at least one antioxidant is coenzyme Q-10.

15. A method of activating a subjects glymphatic system, comprising the step of administering a therapeutically effective amount of the composition of claim 12 by a route of administration that substantially avoids first pass metabolism.

* * * * *